United States Patent [19]

Yoshikumi et al.

[11] 4,401,592

[45] * Aug. 30, 1983

[54] PHARMACEUTICAL COMPOSITION HAVING ANTITUMOR ACTIVITY

[75] Inventors: Chikao Yoshikumi, Kunitachi; Takayoshi Fujii, Tokyo; Masahiko Fujii, Tokyo; Kenichi Matsunaga, Tokyo; Yoshiharu Oguchi, Yono; Koichi Niimura, Sayama, all of Japan

[73] Assignee: Kureha Kagaku Kogyo Kabushiki Kaisha, Nihonbashi, Japan

[*] Notice: The portion of the term of this patent subsequent to Feb. 16, 1999 has been disclaimed.

[21] Appl. No.: 321,486

[22] Filed: Nov. 16, 1981

Related U.S. Application Data

[63] Continuation-in-part of Ser. No. 103,474, Dec. 14, 1979, Pat. No. 4,315,851.

[30] Foreign Application Priority Data

Dec. 29, 1978 [JP] Japan .................................. 53-161388
Nov. 2, 1979 [JP] Japan .................................. 54-142152
Nov. 2, 1979 [JP] Japan .................................. 54-142153

[51] Int. Cl.³ ........................ A61K 39/44; C07G 7/00
[52] U.S. Cl. ............................ 260/112 B; 260/112 R; 424/85
[58] Field of Search ...................... 260/112 R, 112 B; 424/85

[56] References Cited

U.S. PATENT DOCUMENTS

| | | | |
|---|---|---|---|
| 3,917,818 | 11/1975 | Botes ........................................ | 424/87 |
| 3,947,352 | 3/1976 | Cuatrecasas et al. ....... | 260/112 R X |
| 3,983,001 | 9/1976 | Coupek et al. ............... | 260/112 R X |
| 4,017,471 | 4/1977 | Davies .............................. | 260/112 B |
| 4,046,722 | 9/1977 | Rowland ...................... | 260/112 B X |
| 4,093,607 | 6/1978 | Sela et al. .................... | 260/112 R X |
| 4,123,427 | 10/1978 | Daniel ......................... | 260/112 R X |
| 4,160,018 | 7/1979 | Bjorklund ............................. | 424/12 |
| 4,195,017 | 3/1980 | Bogoch ........................... | 260/112 R |
| 4,223,005 | 9/1980 | Teodoresev et al. ............. | 435/7 X |
| 4,228,237 | 10/1980 | Hevey et al. ............................ | 435/7 |
| 4,263,279 | 4/1981 | Sela et al. .............................. | 424/85 |
| 4,275,000 | 6/1981 | Ross .................................. | 260/112 R |
| 4,315,851 | 2/1982 | Yoshikumi et al. ............. | 260/112 B |

FOREIGN PATENT DOCUMENTS

| | | |
|---|---|---|
| 300193 | 1/1970 | Austria . |
| 2312259 | 12/1976 | France . |
| 2323147 | 4/1977 | France . |
| 2362119 | 3/1978 | France . |
| 548776 | 5/1974 | Switzerland . |
| 572745 | 2/1976 | Switzerland . |
| 1509707 | 5/1978 | United Kingdom . |
| 1541436 | 2/1979 | United Kingdom . |

OTHER PUBLICATIONS

Nature, vol. 255, (1975), pp. 487, 488.
Microbiology Abstracts—Section B Bacteriology, vol. 8, No. 5, (1973), 8B4386 p. 164.
Febs Letters, vol. 28, No. 1, (1972), pp. 73–76.
J. Immunol. 113, pp. 948–953, Davphinee et al., (1974).
Cancer Research, 35, pp. 1182–1186 (1975), Levy et al.
Clin. Chem. 22/6, pp. 726–732 (1976), Broughton et al.
Science, vol. 169, 1970, pp. 68–70, Moolten et al.

*Primary Examiner*—Howard E. Schain
*Attorney, Agent, or Firm*—Wegner & Bretschneider

[57] ABSTRACT

Disclosed is a novel pharmaceutical composition having antitumor (anti-cancer) activity without causing pyrexia and anaphylaxis, formed by an amide bonding between an antibody obtained by the purification of the antibody to tumor (cancer) antigen via affinity-chromatography and an antitumor substance (anti-cancer drug).

9 Claims, 12 Drawing Figures

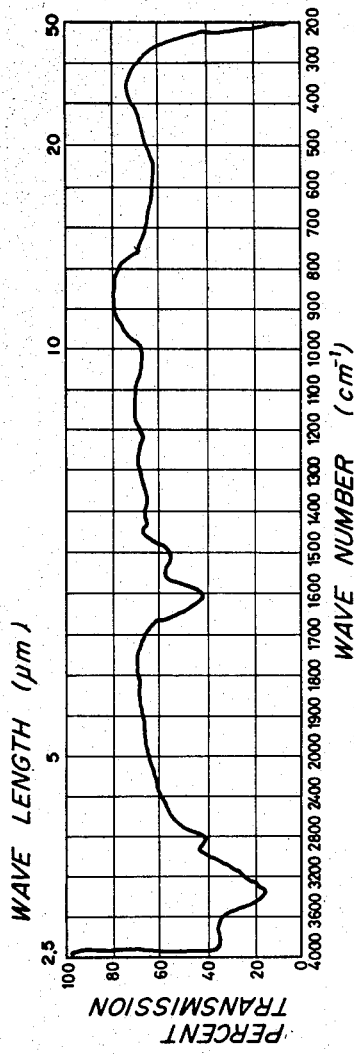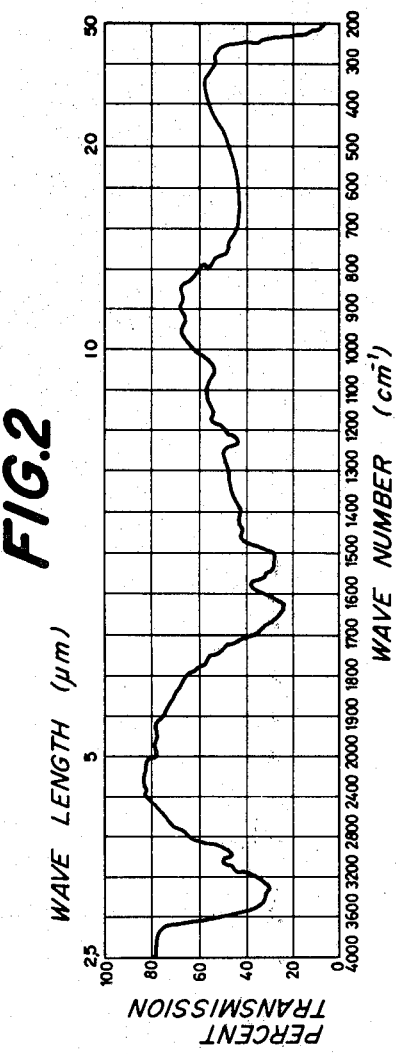

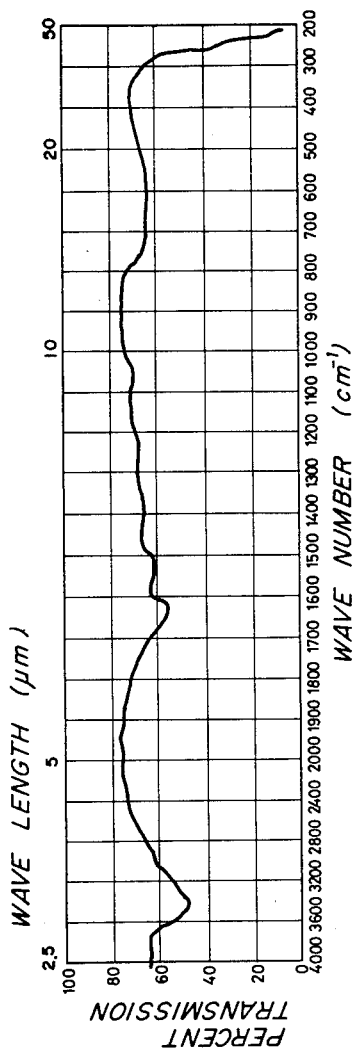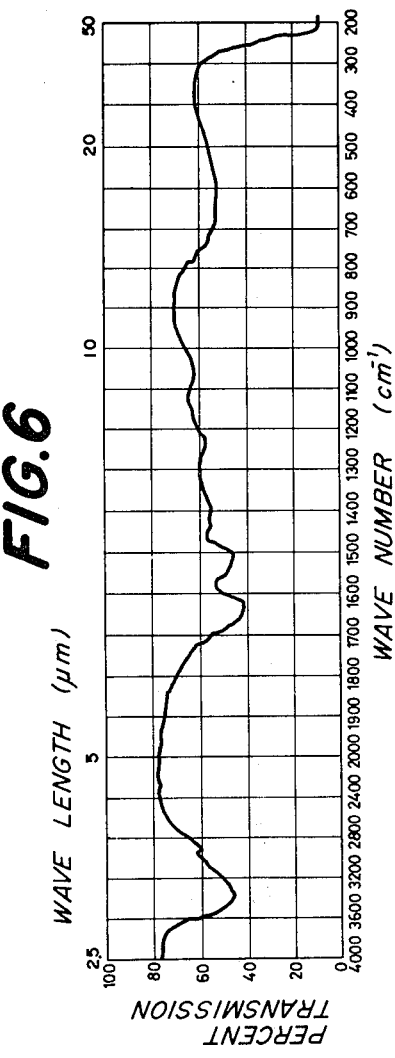

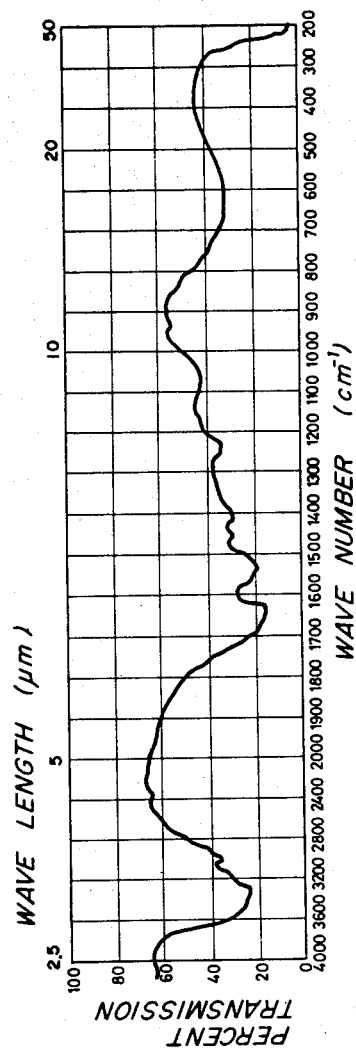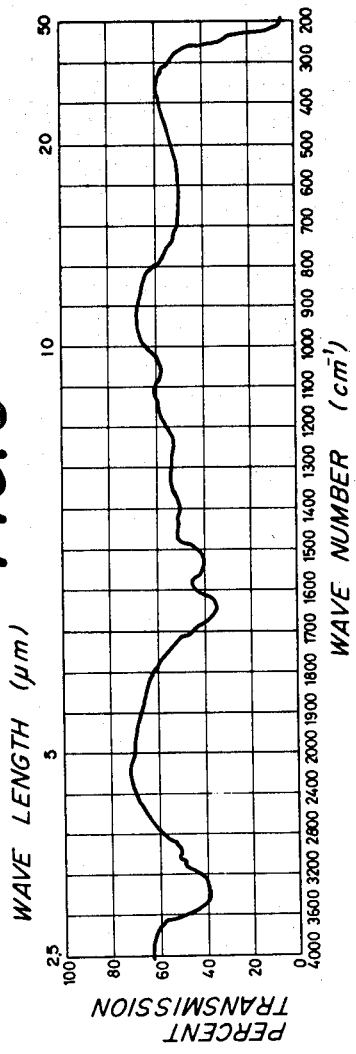

PHARMACEUTICAL COMPOSITION HAVING ANTITUMOR ACTIVITY

CROSS-REFERENCE TO RELATED APPLICATION

This application is a continuation-in-part of application Ser. No. 103,474 filed Dec. 14, 1979, now U.S. Pat. No. 4,315,851.

SUMMARY OF THE INVENTION

The present invention relates to a pharmaceutical composition formed by an amide bonding between a highly pure antibody to tumor (especially, cancer) antigen and an antitumor substance (antineoplastic agent).

The first characteristic aspect of the present invention is to provide a pharmaceutical composition which does not cause side effects such as pyrexia and anaphylactic shock when administered.

The second characteristic aspect of the present invention is to provide an extremely pure antibody to tumor (cancer) antigen, which is suitable for preparation of the above-mentioned pharmaceutical composition.

BACKGROUND OF THE INVENTION

Although recently, several kinds of pharmaceutical composition have been proposed and put into practical use, almost of them exhibit side effects such as leukocytopenia, alopecia and gastrointestinal disturbances. Accordingly, in actual fact, their application is restricted to an extent.

More recently, the application of a substance obtained by chemically bonding an antibody to tumor (cancer) antigen [hereinafter referred to an antitumor-antibody (anti-cancer-antibody)] with an antitumor substance (anti-cancer drug), as an anti-tumour agent, has been tried. However, since the antitumor-antibody (anti-cancer-antibody) used for such a substance is not sufficiently purified, to remove general immunoglobulin and so it could not be recognized as a pure antitumor-antibody (anti-cancer-antibody). Accordingly, in the case where such a substance obtained by bonding such an antitumor-antibody (anti-cancer-antibody) with an antitumor substance (anti-cancer drug) is administered as an anti-tumour agent, the occurrence of pyrexia and anaphylactic shock caused by immunoglobulin contained in the above-mentioned antitumor-antibody (anti-cancer-antibody) is inevitable.

The inventors taking into consideration of the above-mentioned technical backgrounds have examined the elimination of side effects observed in the use of antitumor-antibody (anti-cancer-antibody) and as a result, have confirmed that the extremely pure antitumor-antibody (anti-cancer-antibody) is obtained by purifying the immunoglobulin fraction of the antiserum with an affinity-chromatographic technique and that a pharmaceutical composition obtained by bonding the above-mentioned purified antibody to an antitumor substance (anti-cancer drug) having at least one amino group or carboxyl group does not exhibit the above-mentioned side effects.

Accordingly, an object of the present invention is to supply a pharmaceutical composition having low cytotoxicity and on the other hand excellent antitumor activity (especially, anti-cancer activity). Also an another object of the present invention is to supply an antitumor-antibody (anti-cancer-antibody) with a high purity and a method for preparing the same.

BRIEF EXPLANATION OF DRAWINGS

FIG. 1 of DRAWINGS shows an infrared absorption spectrum of a composition obtained by bonding a purified antisarcoma-180 antibody from a mouse to mitomycin C according to the present invention;

FIG. 2 shows an infrared absorption spectrum of the purified antibody obtained by the purification with affinity-chromatography of an antiserum collected from a male patient suffering from the rectal cancer;

FIG. 5 shows an infrared absorption spectrum of a composition obtained by bonding a purified anti-sarcoma-180 antibody from a rat to chlorambucil according to the present invention;

FIG. 6 shows an infrared absorption spectrum of a composition obtained by bonding a purified anti-sarcoma-180 antibody from rat to uramustine according to the present invention;

FIG. 7 shows an infrared absorption spectrum of a composition obtained by bonding a purified anti-sarcoma-180 antibody from rabbit to cytarabine according to the present invention; and FIG. 8 shows an infrared absorption spectrum of a composition obtained by bonding a purified anti-sarcoma-180 antibody from a mouse to 5-fluorouracil according to the present invention.

DETAILED DESCRIPTION OF THE INVENTION

Figure 4:
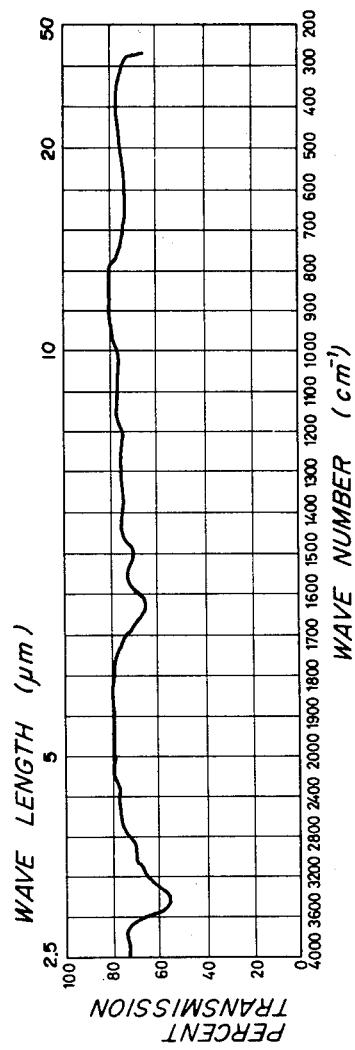
FIG. 4 shows an infrared absorption spectrum of a composition obtained by bonding a purified anti-sarcoma-180 antibody from a mouse to doxorubicin hydrochloride according to the present invention.

The characteristic feature of the present invention resides in that a pharmaceutical composition obtained by bonding a purified antitumor-antibody (especially, anti-cancer-antibody) obtained by purification with affinity-chromatography with an antitumor substance (antineo-plastic agent) having at least one amino group or carboxyl group is used as an active component of the pharmaceutical composition of the present invention.

The antitumor-antibody (anti-cancer-antibody) used in the present invention is obtained by purifying the immunoglobulin fraction induced by the antigen of the tumor (especially, cancers) including sarcoma-180, Sato's lung cancer, L-1210 leukemia, P-388 leukemia, Ehrlich's cancer, Yoshida's sarcoma, acute lymphatic leukemia, medullary cancer, or other human cancers with an affinity-chromatographic technique.

The preparation of the antibody itself to the above-mentioned tumor antigen (especially, cancer antigen) follows the method recorded in "proceedings of the VIth Annual Meeting of Japan Society of Immunology", page 198 (1976) or the method of Dauphin, M. J. et al. (refer to "J. Immunul.", 113, page 948 (1974)). In the former method, using the Freund's complete adjuvant, tumor (cancer) cells are subcutaneously injected into experimental animals to immunize them and the antibody is obtained from the immunized animals. In the latter method, a tumor (cancer) antigen is interaperitoneally injected 3 to 4 times in an animal to immunize the animal and the antibody is obtained from the immunized animal.

In addition, either of the alloantibody and genoantibody may be used in the present invention, however, the use of the alloantibody is preferable.

Hitherto, in order to purify an antibody, the method of, using both the salting-out with ammonium sulfate and the ion-exchange chromatography with DEAE cellulose column, obtaining the immunoglobulin fraction from an antiserum has been frequently utilized. In the present invention, a specifically purifying procedure is carried out by using affinity-chromatography to selectively obtain only the specific antibody to the tumor (cancer) cells from the immunoglobulin fraction obtained by the above-mentioned method. The affinity-chromatography is based on the principle that utilizing a specific affinity between substances of living bodies, for instance, between an enzyme and a substrate or between an antibody and antigen, and then separating one of such pair.

The affinity-chromatography used in the present invention includes (1) a method in which an antigen, extracted from tumor cells (especially, cancer cells) are covalently bonded to a carrier such as agarose gel while using bromocyan and after filling a column with the carrier, a solution of an antibody is passed through the column to bond the antibody to the antigen and then a sufficient amount of a solvent is passed through the column to wash out not-bonded antibody, and a buffer solution at a lower pH is passed through the column to release the bonding between the antibody and the antigen and to eluate the separated antibody, (2) a method in which without using a column, the antibody is made to bond with the antigen by mixing the carrier to which the antigen has been bonded as is described above and a solution of the antibody, and then after washing the carrier particles to remove the not-bonded antibody, the antibody is dissolved out, and (3) a method in which the tumor (cancer) cells themselves are used instead of the carrier to which the antigen is bonded.

Accordingly, the purified antibody obtained in the present invention with the affinity-chromatography is an antitumor (anti-cancer) immunoglobulin with a higher purity than the conventional immunoglobulin fraction, that is, it is a purified antitumor-antibody (anti-cancer-antibody).

The antitumor substance (anti-cancer drug) which are to be bonded by amide bonding with the purified antitumor-antibody (anti-cancer-antibody) obtained as above include the antibiotic substances such as mitomycin C, doxorubicin hydrochloride, bleomycin, daunorubicin, actinomycin D and sarkomycin; the antimetabolitic substances such as cytarabine, 8-azaguanine, 5-fluorouracil, methotrexate and sodium aminopterin; and the alkylating agents such as chlorambucil, melphalan, uramustine, ACNU and cyclophosphamide. Each of the above-mentioned antitumor substance (anti-cancer drug) is publicly known and indicated by a trivial name, their structural formulae being described, for instance, in the following literatures:

"Iyakuhin Yōran (manual of Drugs)", Ed. by Osaka Prefectural Assoc. Hospitals' Pharmacysts. "Biseibutsuyakuhin Kagaku (Chemistry of Drugs derived from Microorganisms)" Ed. by Ueno, Y. et al.

The above-mentioned antitumor substance (anti-cancer drug) is bonded to the above-mentioned antitumor-antibody (anti-cancer-antibody) via the bonding of either the amino group or the carboxyl group in the substance with either the carboxyl group or the amino group in the antibody by bringing the substance into reaction with the antibody under mild conditions. In this case, it is possible to have a more smooth reaction, if necessary, by introducing amino group(s) or carboxyl group(s) into the antitumor substance (anti-cancer drug) in advance. The introduction of the amino- or carboxyl group(s) is preferably carried out by making the antitumor substance (anti-cancer drug) itself or its salt of sodium, potassium or silver into reaction with a compound represented by the general formula of $X(CH_2)_nCOOH$, wherein X represents an atom of chlorine or bromine and n denotes an integer of 1 to 3 or of $HCl.NH_2(CH_2)_nCOX$, wherein X represents an atom of chlorine or bromine and n denotes an integer of 1 to 3, in a water-soluble solvent, for instance, methanol, ethanol, dimethylsulfoxide or dioxane at a temperature of 0° to 50° C., preferably of 10° to 40° C. for 10 minutes to 72 hours. By recrystallizing the thus obtained reaction product from a solvent such as water, an alcohol, chloroform and dioxane a derivative of the antitumor substance (anti-cancer drug), to which amino group(s) or carboxyl group(s) is (are) introduced is obtained. Chloroacetic acid is preferable as the compound represented by the formula of $X(CH_2)_nCOOH$.

The bonding of the purified antitumor-antibody (anti-cancer-antibody) and an antitumor substance (anti-cancer drug) having at least one of amino group or carboxyl group is carried out by dissolving both the two reactants in a water-soluble solvent and adding a reagent as a catalyst to carry out the reaction at a temperature of 0° to 50° C., preferably of 10° to 40° C. for 10 minutes to 8 hours, preferably for 30 minutes to 5 hours and stopping the reaction by the addition of a buffer solution such as acetic acid-sodium acetate.

In the next place, in order to remove the unreacted antitumor substance (anti-cancer drug), the catalyst, components of the buffer solution and salts in the reaction mixture, the reaction mixture is subjected to one of the treatments of dialysis, gelfiltration and ultrafiltration or to a combination of these treatments.

The reagent used in the above-mentioned reaction as the catalyst is selected from the group consisting of thionyl chloride, diethyl phosphorocyanidate and a carbodiimide such as 1-ethyl-3-(3-dimethylaminopropyl)carbodiimide, 1-cyclohexyl-3-(2-morpholinoethyl)carbodiimide, 1-cyclohexyl-3-(4-dimethylaminocyclohexyl)carbodiimide and dicyclohexylcarbodiimide.

On the formation of an amide bond (in this case, —NH—CO—) between the antitumor-antibody (anti-cancer-antibody) and the antibiotic, for example, an antitumor-antibody (anti-cancer-antibody) purified by affinity-chromatography was brought into reaction for condensation with a modified antibiotic prepared by N-acetylating the antibiotic to protect the amino group on the original antibiotic in the presence of the reagent as the catalyst. After purifying the reaction product by dialysis, the dialyzed product was subjected to gel-filtration to obtain fractions. Optical density of the thus obtained respective fractions was determined on the two kinds of light of wave length of 280 and 480 or 360 nm, respectively to obtain a pattern of optical densities of the fractions. The light of 280 nm in wave length is to detect the optical density of the original antitumor-antibody (anti-cancer-antibody), and on the other hand, that of 480 or 360 nm is to detect the optical density of the original antibiotic not N-acetylated.

The same procedure of condensation followed by dialysis and determination of optical density was carried out also on the same antibody and the original antibiotic N-acetylated, and the results of determination of optical density on the fractions of gel-filtration are set forth below.

Figure 9:
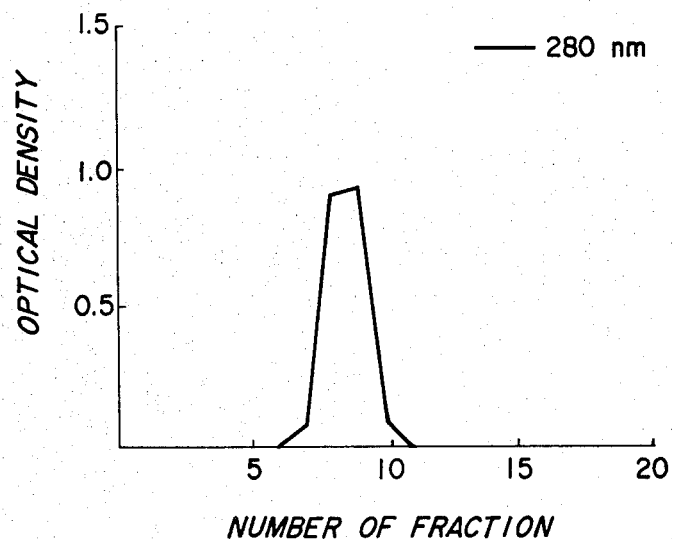
FIG. 9 shows the pattern of optical density to the light of 280 nm of the fractions of the reaction product of the antibody and the modified antibiotic (N-acetyl-daunorubicin).
Figure 11:
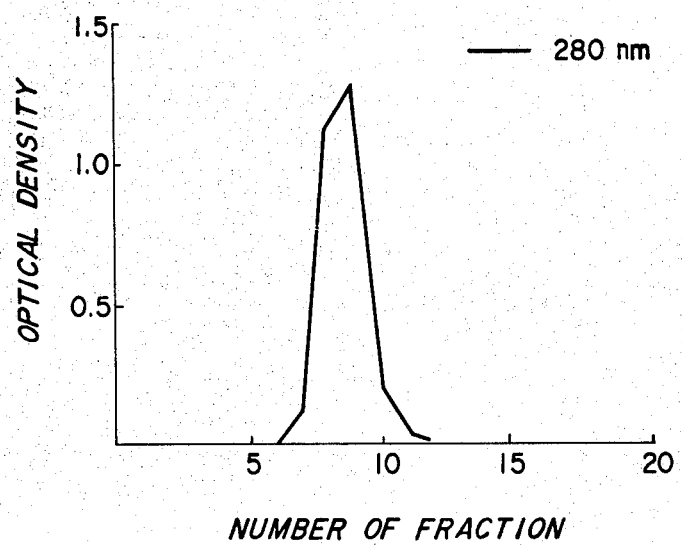
FIG. 11 shows the pattern of optical density to the light of 280 nm of the fractions of the reaction product of the antibody and the modified antibiotic (N-acetyl-mitomycin C).

(1) The pattern of optical density to the light of 280 nm of the fractions of the reaction product of the antibody and the modified antibiotic is quite the same as that of the antibody itself, as are seen in FIG. 9 (in the case of the antibody and N-acetyldaunorubicin) and FIG. 11 (in the case of the antibody and N-acetylmitomycin C).

(2) The pattern of optical density to the light of 480 or 360 nm of the fractions of the reaction product of the antibody and the modified antibiotic did not show any peak as in FIG. 9 (480 nm) and in FIG. 11 (360 nm).

Figure 10:
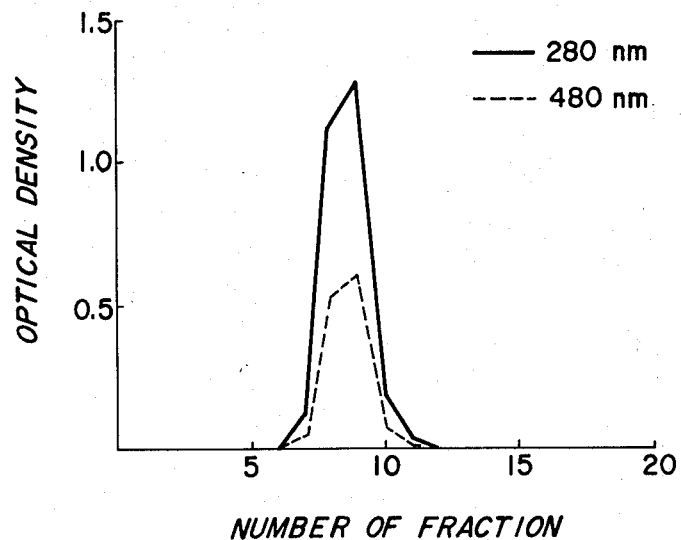
FIG. 10 shows the patterns of optical density of the light of 280 nm (as seen in solid line) and 480 nm (as seen in dotted lines) of the fractions of the reaction product of the antibody and the original (not-acetylated) antibiotic (daunorubicin hydrochloride).
Figure 12:
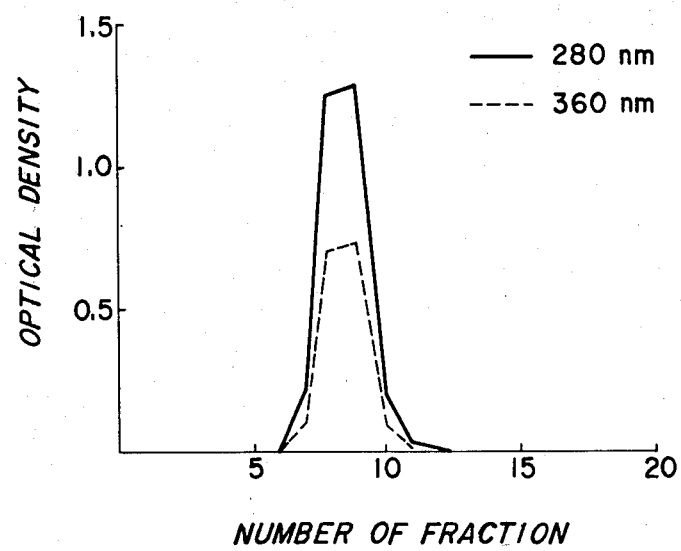
FIG. 12 shows the patterns of optical density of the light of 280 nm (as seen in solid line) and 360 nm (as seen in dotted lines) of the fraction of the reaction product of the antibody and the original (not-acetylated) antibiotic (mitomycin C).

(3) The pattern of optical density of the light of 280 nm of the fractions of the reaction product of the antibody and the original (not-acetylated) antibiotic is quite the same as that of the antibody itself as is seen in the solid line in FIG. 10 or FIG. 12.

(4) The pattern of optical density to the light of 480 or 360 nm of the fractions of the reaction product of the antibody and the original (not-acetylated) antibiotic is quite the same as that of the original (not-acetylated) antibiotic itself, as are seen in the dotted lines in FIG. 10 (480 nm) and FIG. 12 (360 nm).

(5) The position of the peak of the optical density to the ultraviolet light of 280 nm (due to the moiety of the antibody) and that of 480 nm (due to the moiety of daunorubicin hydrochloride) coincided together in FIG. 10, and also the position of the peak of the ultraviolet light of 280 nm (due to the moiety of mitomycin C) coincided together in FIG. 12.

Since the original antibiotic or the modified (N-acetylated) antibiotic not having entered into reaction with the antibody and still remaining in the reaction product was removed from the dialyzate, and although the antibody not having entered into reaction with the original antibiotic or the modified antibiotic still remains in the dialyzate, the facts (1) to (5) lead to the following conclusion.

(a) The fact of (2) shows that there is no moiety showing the same optical property of giving a peak in the pattern of optical density on 480 or 360 nm as that of the original antibiotic or the modified antibiotic, in the fractions of the dialyzed reaction product, and further, in combination of the fact of (1), it is considered that the condensation between the antibody and the modified antibiotic has not taken place, probably by the presence of protected amino group on the modified antibiotic.

(b) On the other hand, the facts of (3) and (4) show that a condensation has taken place between the antibody and the original (not-acetylated) antibiotic, the pattern of optical density of the fractions on 480 or 360 nm showing the presence of the antibiotic's moiety in the condensate of the antibody and the antibiotic.

(c) Accordingly the purified antitumor-antibody (anti-cancer-antibody) and the original antibiotic have entered into chemical condensation between the two based on the amino group of the antibiotic and such a chemical condensation is believed to be due to an acid amide bond, —NH—CO—.

In the pharmaceutical composition obtained by the above-mentioned reaction the antibody and the antitumor substance (anti-cancer drug) are bonded by (an) amide bond(s), and the molecular ratio of antibody to antitumor substance (anti-cancer drug) is 1:2 to 5 in cases where the antitumor substance (anti-cancer drug) is of antibiotic origin and is 1:1 to 10 in cases where it is of antimetabolitic or alkylating origin.

The followings are the explanation of the toxicological specificity, the pharmacological effects and the preparation of the bonded substance, the pharmaceutical composition of the present invention, having an amide bonding between the above-mentioned antitumor-antibody (anti-cancer-antibody) and the antitumor substance (anti-cancer drug).

The acute toxicity was examined by intravenation of 300 mg of the pharmaceutical composition per kg of a mouse as the experimental animal. Because no death was observed in the group of treated mice within one week after the treatment, it can be said that the pharmaceutical composition has an adaptability as a medicine.

The pharmaceutical composition, as shown by Examples, is effective to several cancerous diseases such as acute leukemia, malignant lymphoma, carcinoma, sarcoma, malignant ciliated epithelioma, acute myelogenous leukemia, melanoma, acute lymphatic leukemia, myeloma, etc.

As for the method for formulating the preparation of the pharmaceutical composition for use as an antitumor drug (anti-cancer drugs) and the method of administration thereof, the publicly known methods may be applied. As for the method of administration, oral-, injectional- or rectal administration is mentioned, and as for the form on administration, powder, granule, tablet, injection and suppository are included, however, particularly, the administration by injection is preferable. For the preparation of an injection, water-soluble solvents such as physiological saline solution, sterilized water, Ringer's solution, etc., water-insoluble solvents, isotonication agent, analgesic agent, stabilizing agent, antiseptic, suspending agent, buffering agent, emulsifying agent, etc. are optionally used.

As for an instance, 10 mg of the pharmaceutical composition and 50 mg of mannitol are dissolved in distilled water to be 10 ml of an aqueous solution, and after sterilizing the solution by a conventional method the sterilized solution is introduced into a vial for injection, or the solution is directly lyophilized to be an injection which is, on application, diluted with an aqueous physiological saline solution.

The pharmaceutical composition may be included in a preparation at a concentration of, generally 0.01 to 90% by weight, preferably 0.1 to 60% by weight.

Although the amount of administration of the pharmaceutical composition depends upon the state of diseases, it is generally 0.1 to 9 g per day per an adult person, preferably 0.1 to 6 g.

In addition, according to the present invention, since the tumourtropy and antitumor activity (especially, anti-cancer activity) of the antibody and the antitumor activity (anti-cancer activity) of the antitumor substance (anti-cancer drug) which is bonded to the antibody are kept within the pharmaceutical composition without having been lost, the permaceutical composition, when administered, arrives at the target site of the tumor (cancer) effectively and exhibits its antitumor activity (anti-cancer activity). Accordingly, when considered the amount of the pharmaceutical composition as the base, the administration of the pharmaceutical composition containing an amount of the antitumor substance (anti-cancer drug) of one tenth to one twentieth of the amount of the administration of the same antitumor substance (anti-cancer drug) itself exhibits the same degree of inhibition against the proliferation of the tumor (cancer) as the administration of antitumor substance (anti-cancer drug) itself, and the degree of side effects due to the antitumor substance (anti-cancer drug) contained in the pharmaceutical composition as a component is expected to be only one tenth to one twentieth of the degree of side effects due to the preparation comprising the same antitumor substance (anti-cancer drug). These effects are possibly said to be a synergistic effect of favorable properties of the two components of the pharmaceutical composition.

The followings are the concrete explanation of the method for producing and the pharmacological effectiveness of the antitumor agent (especially, anti-cancer agent) of the present invention referring to Examples non-limitative.

EXAMPLE 1

1-1: Preparation and purification of the antibody by utilizing affinity-chromatography (3)

After culturing the cells of ascites-type sarcoma-180 successively cultured using ICR mouse, in an aqueous physiological solution containing mitomycin C at a concentration of 50 microgram/ml for 30 minutes at a temperature of 37° C., the supernatant liquid was removed by centrifugation, and the proliferated cells were washed three times with an aqueous 0.85% physiological saline solution. Freund's complete adjuvant (hereinafter abbreviated as FCA) was admixed with the thus treated cells of sarcoma-180 deprived of its proliferative activity and the mixture was injected subcutaneously into the sole of a rabbit of body weight of 2.9 kg at a rate of $10^8$ cells/animal. The rabbit was immunized by a repeated injection of the cells 2 weeks after the first injection and then the same number of the cells was intravenated to the same rabbit.

After one week of the last injection, the whole blood of the rabbit was collected by a cannula inserted into the carotid artery, and an antiserum was prepared from the blood and purified as follows:

The salted-out fraction formed by the addition of ammonium sulfate in an amount of 20 to 30% by weight of the amount of saturation to 100 ml of the antiserum was collected and re-dissolved in 20 ml of water. This solution was desalted by dialysis against an aqueous 10 mM phosphate buffer solution (hereinafter abbreviated as PBS) at a pH of 7.0 for 72 hours at a temperature of 4° C. (during the procedure, the external dialysis liquid being exchanged every 24 hours). An equal amount of blood cells of a normal ICR mouse, washed 3 times with an aqueous sodium chloride solution was admixed with the desalted solution and the mixture was left to stand for 30 minutes at a temperature of 4° C. for the absorption. The mixture was subjected to centrifugation to obtain a supernatant liquid. The above-mentioned procedure was repeated 4 times, the total times of absorption procedure being 5. The thus obtained antibody is called the pre-purification antibody (generally called as Ig). In the next place, the purification was further carried out according to the following method: To the supernatant solution subjected to the absorption, the same amount of the cells of sarcoma-180 was admixed and then the mixture was left to stand for 30 minutes at a temperature of 4° C. to make the antibody against sarcoma-180 bonded to the cells of sarcoma-180 and the supernatant solution was removed by centrifugation. An aqueous glycine-hydrochloric acid buffer solution of pH of 3.0 was added to the precipitate to release the antibody. The mixture was centrifugated to collect the supernatant solution containing the antibody. After adjusting the pH of the supernatant solution nearly to neutral with the addition of aqueous 0.1 N sodium hydroxide solution, the nearly neutralized solution was dialyzed against PBS at a temperature of 4° C. for 24 hours (external dialysis liquid being exchanged every 8 hours). The thus obtained dialyzed solution is an aqueous solution containing the rabbit's anti-sarcoma-180 antibody.

1-2: Cytotoxicity test against tumor (cancer) cells and normal cells

Cytotoxicity due to the rabbit's anti-sarcoma-180 antibody obtained as described above to the cells was tested under the presence of a complement (guinea pig's serum) as follows:

Each 100 microliters of the above-mentioned aqueous solution of the antibody, and of the three diluted solutions of the antibody to 10 times, 100 times and 1,000 times, respectively, was mixed with 100 microliters of the aqueous suspension of cells of sarcoma-180 or of the splenic cells of a normal ICR mouse (either of the suspensions used Eagle's minimum essential medium as a solvent, containing $5 \times 10^6$ cells/ml), and the mixtures were left to stand for 15 minutes at the room temperature. Then, an aliquot of 100 microliters of a 2 times diluted serum of a guinea pig with Eagle's minimum essential medium (hereinafter referred as MEM) (the diluted serum is referred as a complement) was added to each of the above-mentioned mixture, and the final mixtures were incubated for 30 minutes at a temperature of 37° C. After incubation, the incubated medium was centrifugated to collect cell pellets, and after washing the pellets once with MEM, an aqueous trypanblue solution was added to the pellets to be examined under microscope for the evaluation of mortality of the cells.

The results are shown in Table 1. As is seen in Table 1, when the degree of mortality of the cells (cell-cytotoxicity activity) was classified into 3 levels and indicated by +, + + and + + + (no death is shown by "−"), it is shown very well that although the antibody taken out after purification of the antiserum by the above-mentioned method showed a cytotoxicity to sarcoma-180 cells not so much different from the toxicity of the antibody taken out without purifying the antiserum, the toxicity of the former to the splenic cells of a normal ICR mouse was extremely low not to have killed them. It shows that the purification of the antiserum was suitable for the purpose of the present invention.

TABLE 1

| Times of dilution of aqueous solution of the antibody | | Mortality of Cells | | | |
|---|---|---|---|---|---|
| | | 1 | 10 | 100 | 1000 |
| Before purification of antiserum by affinity chromatography (3) | Cells of sarcoma-180 | +++ | +++ | + | − |
| | Splenic cells of ICR mouse | ++ | + | − | − |
| After purification of antiserum by affinity chromatography | Cells of sarcoma-180 | +++ | +++ | ++ | − |
| | Splenic cells of ICR mouse | + | − | − | − |
| Control (Eagle's MEM) | Cells of sarcoma-180 | − | | | |
| | Splenic cells of ICR mouse | − | | | |

It is added that the splenic cells of a normal ICR mouse used as the representative of normal cells were obtained by at first after extirpation of the spleen, mincing finely the spleen with a pair of tweezers in Engle3 s MEM to pass through a stainless steel netting of 200 mesh, washing the filtrate once with MEM, adding 3 ml of an aqueous tris-(hydroxylmethylamino) methane-buffered 0.75% ammonium chloride solution of pH of 7.4 to the washed filtrate to remove the erythrocytes and washing the thus treated filtrate three times with MEM.

1-3: Purification of the antibody by affinity-chromatography

Since in the method (3) of affinity-chromatography used in 1-1 above-mentioned there are problems in the separation of the pure antibody that the disturbance is still recognized on the mouse's splenic cells, the following purification of the antibody was carried out utilizing a column to which the tumor (cancer) antigen is bonded. At first, purification was performed on the antigen itself.

Cancer cells of ascites-type sarcoma-180 which have been successively cultured using ICR mice was freeze-dried and after adding an aqueous 5 mM potassium phosphate buffer solution of pH of 7.4 the antigen was extracted from the cells for 20 hours. A supernatant solution was collected by centrifugating the mixture for 10 minutes at 65,000 G. The supernatant solution was further centrifugated for 30 minutes at 180,000 G and the thus obtained supernatant was dialyzed against distilled water for 70 hours at a temperature of 4° C. (during the dialysis, the external liquid was exchanged every 24 hours). The dialyzate was further centrifugated at 65,000 G to remove the precipitate, and after adding ammonium sulfate into the thus obtained supernatant solution to make its concentration 2 M, the solution was centrifugated for 10 minutes at 65,000 G to collect the precipitate. The precipitate was dissolved into distilled water, and the solution was dialyzed against distilled water for 72 hours (during the dialysis, the external liquid was exchanged every 24 hours).

The thus obtained antigen of sarcoma-180 was used for preparing the column for affinity-chromatography as follows:

At first, to an agarose gel (Sepharose 4B, product of Pharmacia Japan Co., Ltd.) swollen with water to be 20 ml, the same volume of an aqueous solution of bromocyan at 1 g/ml was added, and after making reaction for 8 minutes while maintaining the pH of the reaction mixture at 11.0 the mixture was filtered with a glass filter to collect the precipitate which was washed on the filter with ice-cooled distilled water and an ice-cooled aqueous 0.5 M sodium hydrogen carbonate solution. Just after the washing, the precipitate was suspended into an aqueous 0.1 M sodium hydrogen carbonate solution. The above-mentioned solution of the purified antigen was added to the suspension and the mixture was stirred overnight to make reaction. The product was filtered with a glass filter and washed with, at first, an aqueous 0.1 M sodium hydrogen carbonate solution, then with distilled water and at last with an aqueous phosphate buffer solution of sodium chloride (0.85%, pH of 7.0). The thus washed reaction product was packed into a glass tube of 13 mm in internal diameter and 15 cm in length to be the column for affinity chromatography. Three milliliters of the solution of antibody (Ig) prepared by the procedure of above-mentioned 1-1 except for the step of bonding with the cells of sarcoma-180 were poured into the column and then an aqueous 5 mM phosphate buffer solution of sodium chloride (0.85%, pH of 7.0) was flowed into the column until protein became undetectable in the effluent, and then an aqueous 0.5 M sodium chloride solution added with an aqueous 50 mM glycine hydrochloride buffer solution was flowed into the column to collect the fraction as the eluate. The eluate was rapidly neutralized with sodium hydrogen carbonate and the neutralizate was dialyzed against an aqueous phosphate buffer solution of sodium chloride (0.85%, pH of 7.0) for 72 hours (the external liquid was exchanged every 24 hours). The dialyzate thus obtained was an aqueous solution of a purified antibody against sarcoma-180 by column affinity-chromatography.

1-4: Cytotoxicity test against tumor (cancer) cells and normal cells

Cytotoxicity due to the rabbit's anti-sarcoma-180 antibody obtained in 1-3 was examined by the method described in 1-2 on the tumor (cancer) cells and normal cells. The results are shown in Table 2.

TABLE 2

| Times of dilution of the antibody | | Mortality of Cells | | | |
|---|---|---|---|---|---|
| | | 1 | 10 | 100 | 1000 |
| Solution of the antibody after purification by column-affinity chromatography (3) | Cells of sarcoma-180 | +++ | +++ | ++ | − |
| | Cells of spleen of mouse | + | − | − | − |
| Solution of the antibody after purification by column-affinity chromatography (1) | Cells of sarcoma-180 | +++ | +++ | ++ | + |
| | Cells of spleen of mouse | − | − | − | − |
| Control (Eagle's MEM, only) | Cells, sarcoma | − | | | |
| | Cells, splenic | − | | | |

The tabulated results in Table 2 show the reduction of toxicity to the splenic cells and the accentuation of the activity to the cells of sarcoma-180 of the antibody owing to the purification of the antibody by affinity-chromatography (1), that is, show the excellent purification of the antibody by affinity-chromatography (1).

1-5: Bonding between the anti-sarcoma-180 antibody and an antitumor substance (anti-cancer drug)

1-5-1

The anti-sarcoma-180 antibody of rabbit prepared and purified according to the method of 1-1 mentioned before and was made to react with each of the antitumor substance (anti-cancer drug) such as mitomycin C, daunorubicin, bleomycin, actinomycin D, sarcomycin and doxorubicin hydrochloride to produce each substance. As an example, the reaction of the antibody prepared in 1-1 and mitomycin C is described as follows:

To an aqueous solution containing the purified rabbit's anti-sarcoma-180 antibody at a concentration of 10.4 mg/ml, 13.0 mg of mitomycin C was added, and under agitation while adjusting the pH of the solution to 4.75, 3.7 mg of 1-ethyl-3-(3-dimethylaminopropyl) carbodiimide hydrochloride was added to make react for the period indicated in Table 3 and the reaction was stopped by the addition of 2 ml of an aqueous acetic acid-sodium acetate buffer solution of pH of 4.70. After dialyzing the reaction mixture against 5 liter of distilled water at a temperature of 4° C. for 72 hours (during the dialysis, the external liquid was exchanged 3 times), the inner dialysis liquid was condensed and flowed into a column of 1.5 cm in diameter and 55 cm in height packed with a dextrin derivative (Sephadex G-25, prepared by Farmacia Japan Co. Ltd.) to have low-molecular substances in the reaction mixture completely adsorbed onto the column and the eluate was freeze-dried at a temperature of −20° C. to obtain the product. The amount of mitomycin C bonded to the antibody was determined as time passed by using ultraviolet absorption spectroscopy, the results being shown in Table 3.

TABLE 3

Amounts of bonded Mitomycin C to the Antibody

| Reaction time (minute) | Amount of Mitomycin C/anitbody (microgram/mg) |
|---|---|
| 10 | 4.2 |
| 30 | 8.4 |
| 60 | 10.0 |

The thus obtained product, one of the substance of the pharmaceutical composition of the present invention is a modified protein of a molecular weight of about 150,000, soluble in water and insoluble in organic solvents such as benzene, acetone, methanol, etc. This compound shows an infrared absorption spectrum as shown in FIG. 1. In an ultraviolet absorption spectrum, the specific absorption peaks at 280 and 360 nm were seen.

According to the above-mentioned procedures, the purified rabbit's anti-sarcoma-180 antibody obtained in 1-1 (10 mg) was made to react with each of doxorubicin hydrochloride, daunorubicin and actinomycin D to obtain each of the bonded compounds of about 7 mg. The amounts of doxorubicin hydrochloride bonded to 1 mg of the antibody protein were 4.1 microgram and 9.0 microgram, respectively for the time of reaction of 10 and 30 minutes. The same results were obtained by the use of IgG antibody.

1-5-2

The following is an example wherein the anti-sarcoma-180-antibody of rabbit prepared and purified by the method of 1-3 was used in the presence of another carbodiimide, 1-cyclohexyl-3-(4-dimethylaminocyclohexyl)carbodiimide.

Into 10 ml of an aqueous solution containing 100 mg of the above-mentioned antibody, 10 mg of mitomycin C and 5 mg of 1-cyclohexyl-3-(4-dimethylaminocyclohexyl)carbodiimide were added, and after bringing the mixture into reaction for the undermentioned time period, the reaction was stopped by the addition of 3 ml of an acetic acid-sodium acetate buffer solution of pH of 4.7. The reaction mixture was then subjected to dialysis against each 10 liters of distilled water for 72 hours at 4° C. while changing the external liquid 3 times. After condensing the dialyzate, the condensate was passed through a column of 1.6 cm in diameter and 90 cm in height filled with Caphadex G-200 to remove the substances with low molecular weight from the dialyzate by adsorption onto Sephadex and the eluate was lyophilized at −20° C. to obtain the object substance, the combined amount of mitomycin C with the antibody being determined by the absorbency of an aqueous solution of the product at 360 nm and shown below.

| Reaction time (min) | Amount of mytomycin C combined to the antibody (microgram/mg) |
|---|---|
| 10 | 4.0 |
| 30 | 7.1 |
| 60 | 13.2 |

The physicochemical properties of the thus obtained product were almost the same as those obtained in 1-5-1.

Compounds bonded respectively to daunorubicin, bleomycin, actinomycin D, sarcomycin and doxorubicin hydrochloride were synthesized according to the above-mentioned method under the similar conditions as above. The following is an example wherein sarcomycin was bonded to the antibody prepared and purified by the method in 1-3:

1-5-3

Into 20 ml of an aqueous solution of the antibody at a concentration of 10 mg/ml, a reaction mixture prepared by adding 141 mg of 1-ethoxycarbonyl-2-ethoxy-1,2-dihydroquinoline into a solution of 100 mg of sarkomycin into 2 ml of dioxane and stirring the mixture for 2 hours was slowly dopped. After leaving the mixture for a night at 4° C. to react, the reaction mixture was subjected to dialysis against each 20 liters of distilled water while exchanging the external liquid every 8 hours. The dialyzate was passed through a column of 1.6 cm in diameter and 90 cm in height filled with Sephadex G-100 to remove the substances of low molecular weight by adsorption onto Sephadex, and the eluate was lyophilized at −20° C. to obtain the product.

EXAMPLE 2

2-1: Preparation of an antibody to tumor (cancer) cells and purification of the same Ascites-type sarcoma-180 cells successively cultured using ICR mice and deprived of their proliferative activity by mitomycin C were intraperitoneally injected into an ICR mouse once per week at a rate of $10^7$ cells/animal in total 4 times and on the 7th day of the last injection, the blood was collected from the mouse's abdominal large vein on its laparotomy under anesthesia, and an antiserum was prepared from the blood in an amount of 53 ml from 100 animals. The collection of the antibody from the antiserum and the purification of the antibody were performed following 1-1 and the procedure was stopped after absorption by mouse's erythrocytes.

2-2: Purification of an antibody by affinity-chromatography

To 30 g of the freeze-dried ascites-type sarcoma-180 cells successively cultured by using ICR mice, an aqueous solution 3MKCl solution buffered with an aqueous 5 mM potassium phosphate buffer solution of pH of 7.4 was added to extract the antigen for 20 hours. The extract was centrifugated for 10 minutes at 65,000 G to collect the supernatant liquid and the supernatant liquid was further centrifugated for 30 minutes at 180,000 G to collect the supernatant liquid. It was dialyzed against distilled water at a temperature of 4° C. for 72 hours (during the dialysis, the external liquid was exchanged every 24 hours).

The affinity-chromatography of the thus obtained antigen of sarcoma-180 was carried out as follow:

Twenty milliliters of water-swollen agarose gel (Sepharose 4B, Farmacia Japan Co., Ltd.) were mixed with 20 ml of an aqueous bromocyan solution at a concentration 1 g/ml while keeping the pH of the mixture at 11.0 for 8 minutes to bring it into reaction, and the reaction mixture was filtered by a glass filter. The separated filtrate was washed with ice-cooled distilled water and ice-cooled aqueous 0.5 M sodium hydrogen carbonate solution on the filter and at once it was suspended in an aqueous 0.1 M sodium hydrogen carbonate solution and the above-mentioned purified antigen solution was added to the suspension while stirring overnight at the room temperature to make them react. The product was filtered by a glass filter and washed with at first an aqueous 0.1 M sodium hydrogen carbonate solution, then distilled water and at last with an aqueous phosphate buffer solution of sodium chloride (0.85%, pH of 7.0). The washed product was packed into a glass tube of 13 mm in inner diameter and 15 cm in height to be a column for affinity-chromatography.

Three milliliters of the antiserum made by the procedure in 2-1 described before (including an antibody) was flowed into the affinity-chromatographic column, and then an aqueous 5 mM phosphate buffer solution of sodium chloride (0.85%, pH of 7.0) was flowed into the column until protein became undetectable in the effluent, and an aqueous 0.5 M sodium chloride solution added with an aqueous 5 mM glucin-hydrochloric acid buffer solution (pH of 4.0) was flowed into the column to collect the eluate fraction. The eluate fraction, after neutralized with sodium hydrogen carbonate, was at once dialyzed against an aqueous phosphate buffer solution of sodium chloride (0.85%, pH of 7.0) for 72 hours (during dialysis, the external liquid was exchanged every 24 hours). The aqueous solution of an antibody to sarcoma-180 purified by the use of affinity-chomatography was thus obtained.

2-3: Cytotoxicity test against cancer cells and normal cells

Cytotoxicity due to mouse's sarcoma-180 antibody was examined by the method as in Example 1, the results being shown in Table 4.

TABLE 4

| | Mortality of Cells | | | | |
|---|---|---|---|---|---|
| Times of dilution of the antibody | | 1 | 10 | 100 | 1000 |
| Solution of anitbody before purification by affinity chromatography (1) (2-1) | Cells of sarcoma-180 | +++ | ++ | − | − |
| | Cells of spleen of mouse | − | − | − | − |
| Solution of anitbody after purification by affinity chromatography (1) (2-2) | Cells of sarcoma-180 | +++ | +++ | ++ | + |
| | Cells of spleen of mouse | − | − | − | − |
| Control (Eagle's MEM) | Cells of sarcoma-180 | − | | | |
| | Cells of spleen of mouse | − | | | |

As is seen in Table 4, the activity to sarcoma-180 cells has been raised remarkably by affinity-chromatography as mentioned before.

2-4: Bonding of mouse's anti-sarcoma-180 antibody with an antitumor substance (anti-cancer drug)

Mouse's anti-sarcoma-180 antibodies obtained by 2-1 and 2-2, respectively were bonded to mytomycin C by the method described in 1-5, the two substances being bonded with an amide bonding. By the same method, each of doxorubicin hydrochloride, bleomycin, daunorubicin, actinomycin D and sarcomycin was bonded to the antibody with an amide bonding. The pharmaceutical compound obtained as above showed almost the same physicochemical properties as the corresponding compound obtained in 1-5. In Example 3, the representative compounds obtained in 1-5 and 2-4, respectively were examined on their antitumor activity (anti-cancer activity).

EXAMPLE 3

Antitumor activity (anti-cancer activity) of the pharmaceutical composition against solid-type sarcoma-180

Cells of mouse's sarcoma-180 successively cultured by using ICR mice were transplanted subcutaneously to axilla of each group of ICR mouse, the group being consisted of 10 animals, at a rate of $1 \times 10^6$ cells/animal. From after 24 hours of the transplantation, intraperitoneal injection of each of the following agents was carried out once every other day in total ten times and after 5 days of the last injection all the mice were sacrificed to extirpate the cancer. The averaged weight of the cancers ($\overline{T}$) was compared to that ($\overline{C}$) of 10 mice administered with an aqueous physiological saline solution instead of the agent in the following formula to show the rate of inhibiting the proliferation of the cancer (sarcoma-180) by the agent:

$$1 - \overline{T}/\overline{C} \times 100$$

in Table 5, 6, 7 and 8. The above-mentioned agents were: (1) antibodies, (2) commercial antitumor substances (anti-cancer drugs), (3) pharmaceutical composition of rabbit's anti-sarcoma-180 antibody bound to each of commercial antitumor substances (anti-cancer drugs) and (4) pharmaceutical composition of mouse's anti-sarcoma-180 antibody bound to each of commercial antitimor substances (anti-cancer drugs). Table 5 shows pharmaceutical composition synthesized with mitomycin C, Table 6 shows pharmaceutical composition synthesized with bleomycin, Table 7 shows pharmaceutical composition synthesized with doxorubicin and Table 8 shows the results of administration of the antibodies.

TABLE 5

Mitomycin and pharmaceutical composition of Antibodies bound to Mitomycin

| Agent | | Amount of administration (mg/kg) Total | *MMC | Effect of inhibiting Proliferation (%) |
|---|---|---|---|---|
| Mitomycin C | | 1 | 1 | 40 |
| Present Composition | Rabbit's antibody | 5 | 0.05 | 32 |
| | Rabbit's antibody **$A_3$ | 5 | 0.05 | 37 |
| | Rabbit's antibody **$A_1$ | 5 | 0.05 | 40 |
| | Mouse's antibody | 5 | 0.05 | 39 |
| | Mouse's antibody **$A_1$ | 5 | 0.05 | 40 |

Note:
*MMC: Mitomycin, and
$A_1$ or $A_3$: antibody purified by affinity-chromatography (1) or (3)

TABLE 6

Bleomycin and pharmaceutical composition of Antibodies bound to Bleomycin

| Agent | | Amount of administration (mg/kg) Total | Bleomycin | Effect of inhibiting proliferation (%) |
|---|---|---|---|---|
| Bleomycin | | 0.5 | 0.5 | 45 |
| Present Composition | Rabbit's antibody | 5 | 0.05 | 36 |
| | Rabbit's antibody **$A_3$ | 5 | 0.05 | 42 |
| | Rabbit's antibody **$A_1$ | 5 | 0.05 | 45 |
| | Mouse's antibody | 5 | 0.05 | 44 |
| | Mouse's antibody **$A_1$ | 5 | 0.05 | 45 |

TABLE 7

Doxorubicin HCl and pharmaceutical composition of Antibodies bound to Doxorubicin HCl

| Agent | | Amount of administration (mg/kg) Total | **Do. | Effect of inhibiting proliferation (%) |
|---|---|---|---|---|
| Doxorubicin hydrochloride | | 2 | 2 | 50 |
| Present Compound | Rabbit's antibody | 20 | 0.2 | 40 |
| | Rabbit's antibody **$A_3$ | 20 | 0.2 | 47 |
| | Rabbit's antibody **A | 20 | 0.2 | 50 |
| | Mouse's antibody | 20 | 0.2 | 49 |
| | Mouse's antibody **A | 20 | 0.2 | 50 |

Note:
**Do.: Doxorubicin hydrochloride

TABLE 8

| Antibody | Antibodies Amount of administration (mg/kg) | Effect of inhibiting proliferation (%) |
|---|---|---|
| Rabbit | 5 | 4 |

TABLE 8-continued

| Antibody | Antibodies Amount of administration (mg/kg) | Effect of inhibiting proliferation (%) |
|---|---|---|
| | **$A_3$ | 5 | 5 |
| | **$A_1$ | 5 | 5 |
| Rabbit | | 20 | 5 |
| | **$A_3$ | 20 | 5 |
| | **$A_1$ | 20 | 5 |
| Mouse | | 5 | 6 |
| | **$A_1$ | 5 | 7 |
| Mouse | | 20 | 7 |
| | **$A_1$ | 20 | 7 |

$A_1$ or $A_3$: Antibody purified by affinity chromatography (1) or (3)

As are seen in Tables 5 to 7, the rate of inhibition of proliferation of sarcoma-180 of the pharmaceutical composition is, in actual state, nearly the same as that of commercial antitumor substances (anti-cancer agents) at a dose rate of 5 to 10 times of the dose rate of commercial antitumor substances (anti-cancer agents). This fact shows that the antitumor activity (anti-cancer activity) of the antibody itself does not appear substantially and it is really natural. The characteristic of the pharmaceutical composition becomes clear when the amount of administration of commercial antitumor substance (anti-cancer agent) is compared to amount of commercial antitumor substance (anti-cancer agent) as one of the components of the pharmaceutical composition. That is, although the amount of the latter is only one tenth or one twentieth of that of the former, the inhibiting effects are almost the same in both cases. The above-mentioned fact is the reflection that the antibody which is one of the components of the pharmaceutical composition well brings the small amount of commercial anti-cancer agent which is also one of the components of the pharmaceutical composition to the cancer site, the fact realizing the idea of the present invention.

The pharmaceutical composition owing to the above-mentioned function while reducing the amount of administration of the commercial antitumor substance (anti-cancer agent) which originally has an extremely high side effects to one tenth to one twentieth of the customary amount of administration, exhibits the same degree of cancer inhibiting activity.

In addition, it should be noticed that although the origin of the antibody has no relationship to the rate of inhibition of the proliferation of the cancer, when the known compound produced by bonding the antibody prepared by using a rabbit and ordinarily purified to a commercial antitumor substance (anti-cancer drug) was administered to 10 mice, about 3 animals showed a general spasm and stiffening, one of the signs of anaphylactic shock, while the administration of the pharmaceutical composition produced by bonding the antibody purified by affinity-chromatography to the antitumor substance (anti-cancer drug) only caused a very much reduced occurrence of such an anaphylactic shock. Originally the compound prepared by bonding the antibody derived from mouse and purified by ordinary method to the antitumor substance (anti-cancer drug) caused the anaphylactic shock extremely rarely, but when the antibody was further purified by affinity-chromatography, anaphylactic shock was never observed.

EXAMPLE 4

4-1: Preparation of an antibody and purification thereof by using affinity-chromatography Cells of Yoshida's sarcoma successively cultured using Donryu rats were suspended in an aqueous physiological saline solution and after adding mitomycin C (50 microgram/ml) to the suspension, the mixture was incubated for 30 minutes at a temperature of 37° C. and centrifugated to remove the supernatant liquid. The cells were washed three times with an aqueous 0.85% physiological saline solution. Freund's complete adjuvant (hereinafter abbreviated as FCA) was admixed with the cells of Yoshida's sarcoma thus deprived of proliferative activity, and the mixture was subcutaneously injected into the sole of a rabbit of a body weight of 2.9 kg at a rate of $10^8$ cells/animal. After 2 weeks of the first injection, the second injection of the cells was carried out on the same rabbit with the similar method to immunize the rabbit and after two weeks of the second injection, the same cells were intravenated into the same rabbit. After one week of the last injection, the whole blood was collected from the rabbit via the canula inserted into the caroted artery. The antiserum prepared from the blood was purified as follows: That is, to 100 ml of the antiserum an amount of ammonium sulfate corresponding to 20 to 30% by weight of saturation was admixed to effect the salting out. The salted-out fraction was re-dissolved into 20 ml of water, and the thus formed solution was dialyzed against an aqueous 10 mM phosphate buffer solution of sodium chloride (hereinafter referred as PBS) of pH of 7.0 at a temperature of 4° C. for 72 hours (during the dialysis, the external liquid was exchanged every 24 hours). An equal amount of erythrocytes of a normal Donryu rat washed three times with an aqueous sodium chloride solution was admixed with the dialyzate and after leaving to stand for 30 minutes at a temperature of 4° C. the mixture for absorption, it was centrifugated to obtain a supernatant liquid. The above-mentioned procedure of absorption was repeated 4 times, the total times of absorption being 5 times. The thus obtained antibody is called as the pre-purification antibody (commonly called as Ig).

In the next place, the IgG was further purified by the following method: That is, to the supernatant liquid subjected to the absorption five times, an equal amount of the cells of Yoshida's sarcoma was admixed, and the mixture was left to stand for 30 minutes at a temperature of 4° C. to bond the antibody against Yoshida's sarcoma to the cells of Yoshida's sarcoma and then the mixture was centrifugated to remove the supernatant liquid. To the precipitate, an aqueous glycine hydrochloride buffer solution of pH of 3.0 was added to release the antibody. This mixture was then centrifugated to collect the supernatant liquid containing the antibody and the supernatant liquid was treated with an aqueous 0.1 M sodium hydroxide solution to nearly neutral and dialyzed against PBS for 24 hours at a temperature of 4° C. (the external dialysis liquid was exchanged every 8 hours). The thus obtained dialyzate is an aqueous solution of rabbit's anti-Yoshida's sarcoma antibody.

4-2: Cytotoxicity test against tumor (cancer) cells and normal cells

Cytotoxicity due to the rabbit's anti-Yoshida's sarcoma immuno-antibody against cells in the presence of a complement (serum of a guinea pig) was examined as follows: the above-mentioned aqueous solution of the antibody, its 10 times-diluted solution, its 100 times-diluted solution and its 1,000 times-diluted solution were respectively mixed with a suspension of Yoshida's sarcoma cells or a suspension of the splenic cells of a normal Donryu rat (both suspension used Eagle's MEM as a medium and the concentration of the cells was $5 \times 10^6$ cells/ml) at a ratio of 100 microliters: 100 microliters and the mixture was left to stand for 15 minutes to have the antibody absorbed to the cells. And 100 microliters of the serum of a guinea pig diluted with Eagle's MEM to 2 times (the diluted serum is called as a complement) was added to the above-mentioned mixture, and the final mixture was incubated for 30 minutes at a temperature of 37° C. and then centrifugated. The thus obtained precipitate was washed once with Eagle's MEM and after adding the trypaneblue solution the mortality of the cells in the washed and stained precipitate was observed microscopically.

The results of the test are shown in Table 9. As is seen in Table 9, when the mortality of the cells (cell disturbance activity) was classified into 3 levels, and indicated by +, ++ and +++ (no death was indicated by "—"), it was observed that although the toxicity of the antibody taken out after purification of the antiserum to the cells of Yoshida's sarcoma was not so much different from the toxicity of the antibody taken out without purification of the antiserum, the former's toxicity to the splenic cells of a normal Donryu rat was extremely low not to kill the rats. This fact indicates that the purification of the antiserum was suitable for the purpose of the present invention.

TABLE 9

| Times of dilution of aqueous solution of antibody | | Mortality of Cells | | | |
|---|---|---|---|---|---|
| | | 1 | 10 | 100 | 1000 |
| Solution of antibody before purification by affinity chromatography (3) | Cells of Yoshida's sarcoma | +++ | +++ | + | — |
| | Cells of spleen of rat | ++ | + | — | — |
| Solution of antibody after purification by affinity chromatography (3) | Cells of Yoshida's sarcoma | +++ | +++ | ++ | — |
| | Cells of spleen of rat | + | — | — | — |
| Control (Eagle's MEM) | Cells of Yoshida's sarcoma | — | | | |
| | Cells of spleen of rat | — | | | |

In addition, the splenic cells of Donryu rat used as the representative of the normal cells were obtained by after extirpation of the spleen, finely crushing the spleen with a pair of tweezers in Eagle's MEM, letting the fragments pass a stainless steel netting of 200 mesh through, washing the passed fragments once with Eagle's MEM, mixing with 30 ml of an aqueous tris-(hydroxylmethylamino) methane buffered 0.75% ammonium chloride solution of pH of 7.4 to destract the erythrocytes in the specimen and washing the fragments three times with Eagle's MEM.

4-3: Purification of an antibody by affinity-chromatography (1)

The following purification of antibody was carried out by affinity-chromatography using a column with a carrier to which a tumor (cancer) antigen has been bonded. At first, the antigen itself was purified as follows: That is, the tumor (cancer) cells of Yoshida's sarcoma successively cultured using Donryu rats were freeze-dried, and to 30 g of this cells an aqueous solution of 3 M KCl buffered with an aqueous 5 mM potassium phosphate buffer solution (pH: 7.4) was added to extract the antigen for 20 hours, and the extract-liquid was centrifugated for 10 minutes at 65,000 G to collect the supernatant liquid and the supernatant liquid was further centrifugated for 30 minutes at 180,000 G to collect the supernatant liquid, which was dialyzed for 70 hours at a temperature of 4° C. (during the dialysis, the external liquid was exchanged every 24 hours). The dialyzate was further centrifugated at 65,000 G to remove the precipitate, and after adding ammonium sulfate to the supernatant liquid to make the concentration to 2 M, the mixture was centrifugated for 10 minutes at 65.000 G to collect the precipitate, which was dissolved into distilled water, and the solution was dialyzed against distilled water for 72 hours (during dialysis, the external liquid was exchanged every 24 hours).

Using the thus obtained antigen of Yoshida's sarcoma, the column for affinity-chromatography was prepared as follows:

To 20 ml of water-swollen agarose gel (Sepharose 4B, made by Farmacia Japan Co., Ltd.) 20 ml of an aqueous bromocyan solution of a concentration of 1 g/ml were added and while keeping the pH at 11.0 the mixture was left to stand for 8 minutes to react each other and the reaction mixture was filtered with a glass filter. The precipitate left on the filter was washed with ice-cooled distilled water and then with ice-cooled aqueous 0.5 M sodium hydrogen carbonate solution followed by dispersing the washed precipitate into an aqueous 0.1 M sodium hydrogen carbonate solution.

The above-mentioned aqueous solution of the purified antigen was added to the dispersion to make the two components react by stirring overnight at the room temperature. The product was filtered with a glass filter and washed at first with an aqueous 0.1 M sodium hydrogen carbonate solution, then with distilled water and at last with an aqueous phosphate buffer solution of sodium chloride (0.85%, pH of 7.0).

The thus washed reaction product was packed in a glass tube of 13 mm in diameter and 15 cm in height to be a column for affinity-chromatography. Into this column, 3 ml of the solution of antibody (Ig) prepared by the procedure of 4-1 above-mentioned (except for the step of bonding with the cells of Yoshida's sarcoma) was flowed and then an aqueous 5 mM phosphate buffered saline (0.85% sodium chloride, pH of 7.0) was introduced into the column until protein became undetectable in the effluent. Then, 50 mM glycin-hydrochloric acid buffered 0.5 M sodium chloride solution (pH of 4.0) was introduced into the column to collect the effluent fraction, which was at once neutralized with sodium hydrogen carbonate and the neutralizate was dialyzed against phosphate buffered saline (0.85% sodium chloride, pH of 7.0) for 72 hours (during the dialysis the external liquid was exchanged every 24 hours). Thus, the aqueous solution of the purified antibody by column affinity-chromatography against Yoshida's sarcoma was obtained.

4-4: Cytotoxicity test against the tumor (cancer) cells and the normal cells

Cytotoxicity due to the anti-Yoshida's sarcoma antibody obtained in 4-3 described above was examined by the same method as in 4-2, the results being shown in Table 10.

TABLE 10

| Times of dilution of the antibody | | Mortality of Cells | | | |
|---|---|---|---|---|---|
| | | 1 | 10 | 100 | 1000 |
| Solution of antibody after purification with affinity chromatography (3) | Cells of Yoshida's sarcoma | +++ | +++ | ++ | — |
| | Cells of spleen of rat | + | — | — | — |
| Solution of antibody after purification with affinity chromatography (1) | Cells of Yoshida's sarcoma | +++ | +++ | ++ | + |
| | Cells of spleen of rat | — | — | — | — |
| Control (Eagle's MEM) | Cells of Yoshida's sarcoma | — | | | |
| | Cells of spleen of rat | — | | | |

The results show that the activity of the antibody to cells of Yoshida's sarcoma was raised remarkably, however that of the antibody to the splenic cells of rat was reduced by the purification with column affinity chromatography, and that the purification with affinity chromatography is excellent.

4-5: Bonding of anti-Yoshida's sarcoma antibody to an antitumor (anti-cancer) alkylating agent Rabbit's anti-Yoshida's sarcoma antibodies prepared and purified in the above-mentioned 4-1 and 4-3 were made to react to one of the commercialized anti-cancer agents, chlorambucil, melphalan (phenyl alanine mustard), ACNU, uramustine and cyclophosphamide to synthesize each of bonded compounds. The followings are the description of the synthetic examples:

SYNTHETIC EXAMPLE 1

Reaction of the antibody with chlorambucil

To 10 ml of an aqueous solution containing the purified rabbit's antibody against Yoshida's sarcoma obtained in 4-1 at a rate of 10.0 mg/ml, 40 mg of chlorambucil was added and under agitation while adjusting the pH of the solution at 4.75 with hydrochloric acid, 25.2 mg of 1-ethyl-3-(3-dimethylaminopropyl) carbodiimide hydrochloride was added to the mixture to perform a reaction for 40 minutes. The reaction was stopped by adding 20 ml of an aqueous acetic acid-sodium acetate buffered solution at pH of 4.75.

In the next place, the reaction mixture was dialyzed against 5 liters of distilled water for 72 hours at a temperature of 4° C. (during the dialysis, the external liquid was exchanged three times). After condensing the internal dialysis liquid, the condensate was passed through a column of 3 cm in diameter and 65 cm in height packed with a dextrin derivative (Sephadex G-200, made by Pharmacia Japan Co., Ltd.) to completely separate the high molecular weight substances and the low-molecular weight substances in the solution. The effluent from the column was ultracentrifugated for 60 minutes at 40,000 G, and the supernatant liquid was freeze-dried at −20° C. to obtain the object substance. The protein content of the product was determined by Copper- Folin's method using albumin as the standard, and the bonded amount of the alkylating agent was determined by the method of Epstein (Epstein, J. Anal. Chem., 27, 1423 (1955)). The results showed that in the obtained pharmaceutical composition, 10 micrograms of chlorambucil bonded to 1 mg of the antibody.

SYNTHETIC EXAMPLE 2

Reaction of the antibody with melphalan

In the same manner as in Synthetic Example 1, however, using the same amount of melphalan instead of chlorambucil in Synthetic Example 1, and further using 5 liters of PBS instead of distilled water in dialysis in Synthetic Example 1, the purified rabbit's antibody was bonded to melphalan to obtain a pharmaceutical composition in which 10 micrograms of melphalan bonded to 1 mg of the antibody.

SYNTHETIC EXAMPLE 3

Reaction of the antibody with uramustine

In the same manner as in Synthetic Example 1, however, using 40 mg of uramustine instead of chlorambucin of Synthetic Example 1, the purified rabbit's antibody was made to react with uramustine. However, it was found that uramustine did not bonded substantially to the antibody. Then, chloroacetic acid was made to react to uramustine to raise the reactivity as follows:

To 10 ml of methanol, 500 mg of uramustine and 139 mg of potassium methoxide were dissolved, and 188 mg of chloroacetic acid was added to the solution followed by agitation for 60 minutes at the room temperature. After the reaction was over, the reaction mixture was condensed under reduced pressure. The residue was recrystallized from methanol and chloroform to obtain 215 mg (yield of 35%) of crystals, of which the following structure of an uramustine derivative was confirmed by analyses:

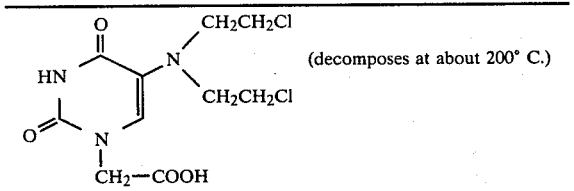

(decomposes at about 200° C.)

| Elementary analysis: | C % | H % | N % |
|---|---|---|---|
| Found: | 38.50 | 4.00 | 13.30 |
| Calcd. as $C_9H_{13}N_3O_4Cl_2$ | 38.70 | 4.19 | 13.54 |

In the next place, the thus obtained derivative of uramustine was made to react with the rabbit's antibody against Yoshida's sarcoma obtained in 4-1 in the same manner as in Synthetic Example 1 to obtain the object pharmaceutical composition in which 10 micrograms of uramustine bonded to 1 mg of the antibody.

SYNTHETIC EXAMPLE 4

Reaction of the antibody with a derivative of melphalan

At first a derivative of melphalan was synthesized from melphalan as follows:

Into 10 ml of dimethylsulfoxide, 200 mg of silver salt of melphalan were dissolved, and 100 mg of chloroacetic acid were added to the solution followed by the agitation for 64 hours while shading light. After removing the precipitate of the reaction mixture, dimethylsulfoxide and chloroacetic acid were distilled off under reduced pressure on a water bath at a temperature of 80° C.

On adding water to the residue and cooling the mixture, white crystals deposited. The deposited crystals were dried under reduced pressure. The thus obtained derivative of melphalan (yield of 40%) was used in the reaction with the antibody obtained in 4-1 by the same procedure in Synthetic Example 2 to make a pharmaceutical composition in which 16 microgram of the derivative of melphalan bonded to 1 mg of the antibody.

SYNTHETIC EXAMPLE 5

The rabbit's antibody against Yoshida's sarcoma, obtained and purified in 4-3 was made to react with each of the following compounds in the same manner as in Synthetic Example 1: chlorambucil, melphalan, a derivative of melphalan (refer to Synthetic Example 4) and a derivative of uramustine (refer to Synthetic Example 3).

The thus synthesized pharmaceutical composition were almost the same as the pharmaceutical composition obtained in the above-mentioned Synthetic Examples.

EXAMPLE 5

5-1: Preparation and purification of an antibody against tumor (cancer) cells

MMc treated cells of ascites-type of Yoshida's sarcoma successively maintained using Donryu rats were immunized once a week into the abdominal cavity of a Donryu rat in total of 4 times, and after 7 days of the fourth immunization the blood was collected from the abdominal large vein of the rat subjected to laparotomy under anesthesia. The antiserum containing the antibody was separated from the blood, the amount being 70 ml from 100 rats. The preparation of the antibody from the antiserum and the purification thereof were performed in the same manner as is 4-1, however, the procedure was stopped after absorption with rat's erythrocytes.

5-2: Purification of the antibody by affinity-chromatography (1)

Into 30 g of lyophilized cells of Yoshida's sarcoma successively maintained by using Donryu rats, an aqueous 3 M KCl solution buffered with an 5 mM potassium phosphate at pH of 7.4 was added to effect the extraction of the antigen for 20 hours. The extract liquid was centrifugated for 10 minutes at 65,000 G to collect the supernatant liquid, which was further centrifugated for 30 minutes at 180,000 G to collect the supernatant liquid. The liquid was dialyzed at a temperature of 4° C. for 72 hours against distilled water (during the dialysis, the external liquid was exchanged every 24 hours).

The procedures of affinity-chromatography performed on the thus obtained antigen of Yoshida's sarcoma was quite the same as the procedures performed on the antigen of sarcoma-180 in 1-3 of Example 1 (1-3).

5-3: Cytotoxicity test against tumor (cancer) cells and normal cells

The cytotoxicity due to the rat's antibody to Yoshida's sarcoma was examined by the same method as in Example 4, the results being shown in Table 11.

TABLE 11

| Times of dilution of aqueous solution of the antibody | Mortality of Cells | | | |
|---|---|---|---|---|
| | 1 | 10 | 100 | 1000 |
| Antibody before purification by affinity chromatography (1) — Cells of Yoshida's sarcoma | +++ | ++ | − | − |
| Antibody before purification by affinity chromatography (1) — Splenic cells of rat | − | − | − | − |
| Antibody after purification by affinity chromatography (1) — Cells of Yoshida's sarcoma | +++ | +++ | ++ | + |
| Antibody after purification by affinity chromatography (1) — Splenic cells of rat | − | − | − | − |
| Control (Eagle's MEM) — Cells of Yoshida's sarcoma | − | | | |
| Control (Eagle's MEM) — Splenic cells of rat | − | | | |

As is seen in Table 11, the activity of the antibody against the cells of Yoshida's sarcoma has been remarkably raised by affinity-chromatography (1) as were in the preceeding Examples.

5-4: Bonding the rat's antibody against Yoshida's sarcoma to antitumor substance (anti-cancer drug)

The rat's antibodies against Yoshida's sarcoma obtained by the procedures in 5-1 and 5-2 were bonded respectively to chlorambucil by the method quite the same as described in 4-5 to obtain pharmaceutical composition having an amide linkage between the two components.

By applying the same method to melphalan, a derivative of melphalan and a derivative of uramustine, respectively, each product having a bonding between the antibody and each of the above-mentioned pharmaceutical composition with an amide linkage was obtained.

All of the thus obtained pharmaceutical composition showed almost the same physicochemical properties as those of the corresponding pharmaceutical composition obtained by the procedures in the above-mentioned 4-5.

EXAMPLE 6

Antitumor (anti-cancer) effect against Yoshida's sarcoma

Cells of Yoshida's sarcoma successively maintained by using Donryu rats were transplanted into the abdominal cavity of all ten rats in each group of Donryu rats at a rate of $1 \times 10^6$ cells/animal, and from after 24 hours of the transplantation each one of the following agents was injected intraperitoneally into each of the rats in groups once every other day in total 10 times. After observing the mortality of the rats, the life-elongating rate of the agent was obtained by calculating the value of dividing the average days of survival of treated rats in one group ($\overline{T}$) by the average days of survival of control ($\overline{C}$) and multiplied by 100, that is, $100 \times \overline{T}/\overline{C}$. The results of the above-mentioned tests are shown in Tables 12 to 16, the agents being chlorambucil and chlorambucil+antibody (Table 12), melphalan and melphalan+antibody (Table 13), a derivative of uramustine and the derivative of uramustine+antibody (Table 14), a derivative of melphalan and the derivative of melphalan+antigen (Table 15) and antibodies themselves (Table 16).

TABLE 12

| Agent | | Amount of administration (mg/kg) | | Life-elongating rate (%) |
|---|---|---|---|---|
| | | Agent | Chlorambucil | |
| | Chlorambucil | 1.0 | 1.0 | 259 |
| Present Composition | Antibody Rabbit | 10.0 | 0.1 | 230 |
| | *Antibody₃ Rabbit | 10.0 | 0.1 | 238 |
| | *Antibody₁ Rabbit | 10.0 | 0.1 | 240 |
| | Antibody Rat | 10.0 | 0.1 | 235 |
| | *Antibody₁ Rat | 10.0 | 0.1 | 245 |

Note:
*shows that the antibody₁ was purified by the technique of affinity-chromatography (1)

TABLE 13

| Agent | | Amount of administration (mg/kg) | | Life-elongating rate (%) |
|---|---|---|---|---|
| | | Agent | Melphalan | |
| | Melphalan | 1.5 | 1.5 | 230 |
| Present Composition | Antibody Rabbit | 15.0 | 0.15 | 230 |
| | *Antibody₃ Rabbit | 15.0 | 0.15 | 237 |
| | *Antibody₁ Rabbit | 15.0 | 0.15 | 240 |
| | Antibody Rat | 15.0 | 0.15 | 230 |
| | *Antibody₁ Rat | 15.0 | 0.15 | 245 |

TABLE 14

| Agent | | Amount of administration (mg/kg) | | Life-elongating rate (%) |
|---|---|---|---|---|
| | | Agent | Uramustine | |
| | Derivative of uramustine | 5 | 5 | 290 |
| Present Composition | Antibody Rabbit | 50 | 0.5 | 260 |
| | *Antibody₃ Rabbit | 50 | 0.5 | 264 |
| | *Antibody₁ Rabbit | 50 | 0.5 | 265 |
| | Antibody Rat | 50 | 0.5 | 270 |
| | *Antibody₁ Rat | 50 | 0.5 | 285 |

TABLE 15

| Agent | | Amount of administration (mg/kg) | | Life-elongating rate (%) |
|---|---|---|---|---|
| | | Agent | Melphalan | |
| | Derivative of melphalan | 1.5 | 1.5 | 230 |
| Present Composition | Antibody Rabbit | 15.0 | 0.24 | 260 |
| | *Antibody₃ Rabbit | 15.0 | 0.24 | 278 |
| | *Antibody₁ Rabbit | 15.0 | 0.24 | 280 |
| | Antibody Rat | 15.0 | 0.24 | 270 |
| | *Antibody₁ Rat | 15.0 | 0.24 | 290 |

Note:
*shows that Antibody₁ or Antibody₃ in Tables 13–15 was purified by affinity chromatography (1) or (3).

TABLE 16

| Antibody | Amount of administration (mg/kg) | Life-elongating rate (%) |
|---|---|---|
| Rabbit* | 5 | 100 |
| | 5 | 105 |
| Rabbit* | 20 | 105 |
| | 20 | 105 |
| Rat* | 5 | 110 |
| | 5 | 120 |
| Rat* | 20 | 120 |
| | 20 | 120 |

Note:
*shows that antibody was purified by affinity chromatography (1) or (3).

As are seen in Tables 12 to 15, the life-elongating rate of the pharmaceutical composition on rats is nearly the same as that of the commercial antitumor substance (anti-cancer drug) when administered at a dose rate of 5 to 10 times of that of the commercial antitumor substance (anti-cancer drug), the fact being natural and showing that the tumor-inhibiting activity (cancer-inhibiting activity) of the antibody itself was not exhibited at the degree of the dose rate (see Table 16). The characteristics of the pharmaceutical composition appear clearly when the amount of administration of the commercial antitumor substance (anti-cancer drug) as a component of the pharmaceutical composition is compared with the amount of administration of such an antitumor substance (anti-cancer drug) itself as the agent. That is, the former is only one tenth or one twentieth of the latter, however, the former gave the substantially same life-elongating rate as the latter. This is the result of the effective translocation of the commercial antitumor substance (anti-cancer drug) to the tumor (cancer) site by the antibody which is another effective component of the pharmaceutical composition, the fact being the realization of the idea of the present invention.

The pharmaceutical composition, owing the above-mentioned function, exhibits the same degree of antitumor-inhibiting activity (cancer-inhibiting activity) in spite of reducing the use of the ordinary commercialized antitumor substance (anti-cancer drug) to one tenth to one twentieth, the side effects of the ordinary commerciallized antitumor substance (anti-cancer drug) being extremely high.

In addition, it should be particularly noted that the occurrence of anaphylactic shock which is experienced in the case where the antibody prepared using rabbits and purified by the usual method was bonded to a commercial antitumor substance (anti-cancer drug) and the bonded substance was administered to rats was very much reduced in the case where the antibody was purified by the procedure of affinity chromatography of the present invention. Such a reduction of the occurrence of anaphylactic shocks has been noticed in the case of the antibody against sarcoma-180 in Example 3, and the advantageous effect of affinity chromatography was exhibited again in the case of against Yoshida's sarcoma. In the case where the antibody prepared using mouse and purified by affinity chromatography, the administration of the pharmaceutical composition produced using the antibody did not exhibit any anaphylactic shocks on rats.

EXAMPLE 7

7-1: Preparation and purification of an antibody against tumor (cancer) cells

Fifty milliliters of the blood were collected from a male patient suffering from the rectal cancer of age of 50, and 22 ml of an antiserum containing an antibody were obtained from the blood.

7-2: Purification of the antibody by affinity-chromatography (1)

To the lyophilized cancer tissue resected from the above-mentioned patient on operation, 50 ml of 3 M potassium chloride solution buffered by a 5 mM potassium phosphate to pH of 7.4 were added to extract the antigen for 20 hours. After centrifugation of the extract liquid for 10 minutes at 65,000 G, the supernatant liquid was collected and dialyzed against distilled water for 72 hours at a temperature of 4° C. (during the dialysis, the external liquid was exchanged every 24 hours). The affinity chromatography of the thus obtained antigen of the patient's tumor (cancer) tissue was carried out in quite the same manner as in 1-3 of Example 1, except only for using the solution of the antiserum containing the antibody obtained in 7-1 from the patient instead of using the antibody obtained from a mouse.

Figure 3:
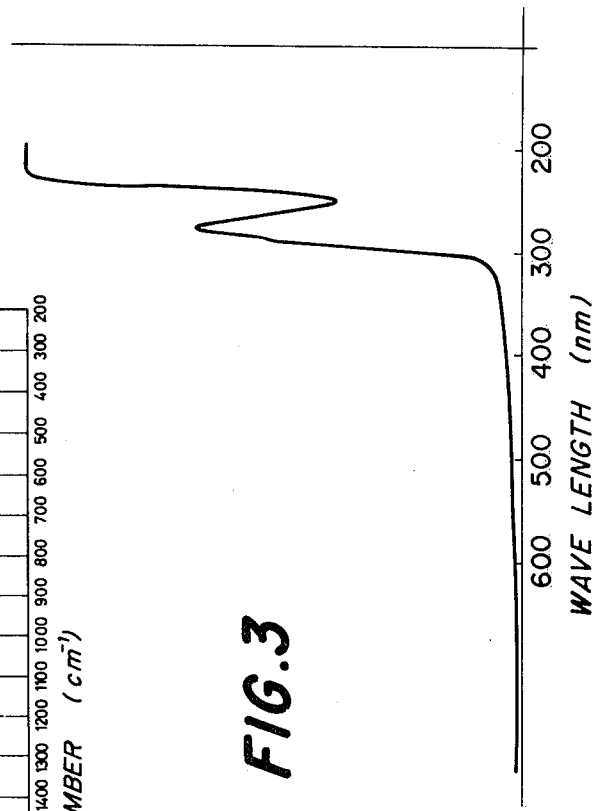
FIG. 3 shows an ultra-violet absorption spectrum of the above-mentioned purified antibody.

The thus obtained antibody was also soluble in water but insoluble in organic solvents such as methanol, ethanol, acetone and benzene and showed the infrared and ultraviolet absorption spectra respectively indicated in FIG. 2 and FIG. 3, having a molecular weight of about 150,000 and presenting at Rf of 0 to 0.1 in disc electropholetic diagram.

EXAMPLE 8

8-1: Preparation and purification of an antibody utilizing affinity chromatography (3)

Mitomycin C (50 microgram/ml) was added to the cells of ascites-type P-388 tumor (cancer) successively maintained by using DBA/2 mice suspended in an aqueous physiological saline solution and after incubating the mixture for 30 minutes at 37° C., the supernatant was removed by centrifugation and the cells were washed 3 times with an aqueous 0.85% physiological saline solution.

The procedures of immunization of the thus treated cells of P-388 tumor (cancer) deprived of proliferative activity, to rabbits and the procedures thereafter to obtain the aqueous solution of rabbit's anti-P 388 tumor (cancer) antibody were quite the same as those in 1-1 of Example 1.

8-2: Cytotoxicity test against tumor (cancer) cells and normal cells

Cytotoxicity due to the thus obtained rabbit's antibody against P-388 tumor (cancer) on cells was examined under the presence of a complement (serum of a guinea pig) by the method already described in 1-2 of Example 1, the results being shown in Table 17.

TABLE 17

| | | Mortality of Cells | | | |
|---|---|---|---|---|---|
| Times of dilution of aqueous solution of antigen | | 1 | 10 | 100 | 1000 |
| Antibody solution before purification by affinity chromatography (3) | Cells of P-388 tumor (cancer) | +++ | +++ | + | — |
| | Cells of spleen of rat | ++ | + | — | — |
| Antibody solution after purification by affinity chromatography (3) | Cells of P-388 tumor (cancer) | +++ | +++ | ++ | — |
| | Cells of spleen of rat | + | — | — | — |
| Control (Eagle's MEM) | Cells of P-388 tumor (cancer) | — | | | |
| | Cells of spleen of rat | — | | | |

In addition, the splenic cells of DBA/2 mouse used as the representative of normal cells were treated by the same procedure as those described in 1-2, Example 1.

8-3: Purification of the antibody by using affinity chromatography (1)

The mouse's anti-P 388 tumor (cancer) antibody was purified using a column with a carrier to which an antigen of P-388 tumor (cancer) has been bonded. The procedures themselves were quite the same as those in 1-3 of Example 1, except for using the cells of P-388 tumor (cancer) successively maintained by using DBA/2 mouse instead of the ascites-type sarcoma-180 cells successively maintained by using ICR mouse.

8-4: Cytotoxicity test against tumor (cancer) cells and normal cells

Cytotoxicity due to the rabbit's anti-P-388 tumor (cancer) antibody was examined by the same method as in 8-2, the results being shown in Table 18.

TABLE 18

| Times of dilution of solution of antibody | | Mortality of Cells | | | |
|---|---|---|---|---|---|
| | | 1 | 10 | 100 | 1000 |
| Solution of antibody after purification by affinity chromatography (3) | Cells of P-388 tumor (cancer | +++ | +++ | ++ | − |
| | Splenic cells of mouse | + | − | − | − |
| Solution of antibody after purification by affinity chromatography (1) | Cells of P-388 tumor (cancer) | +++ | +++ | ++ | + |
| | Splenic cells of mouse | − | − | − | − |
| Control (Eagle's MEM) | Cells of P-388 tumor (cancer) | − | | | |
| | Splenic cell of mouse | − | | | |

The above-indicated results show that the activity of the antibody against P-388 tumor (cancer) cells was remarkably raised and the toxicity of the antibody to the splenic cells was reduced by the purification of affinity chromatography, as in other antibody already mentioned above, indicating the excellent effect of purification due to affinity chromatography (1).

8-5: Bonding of the anti-P-388 tumor (cancer) antibody to antitumor (anti-cancer) antimetabolites The rabbit's anti-P-388 antibodies prepared by the method of 8-1 and 8-3 and purified by their methods were made to react with each of cytarabine, methotrexate and 5-fluorouracil to synthesize the compounds having an amide bonding between the antibody and the antimetabolite. The followings are the examples of bonding:

SYNTHETIC EXAMPLE 6

Into an aqueous solution containing 10.0 mg of the purified rabbit's anti-P-388 cancer antibody in 1 ml, 20.0 mg of cytarabine were added and then 30 mg of 1-ethyl-3-(3-dimethylaminopropyl) carbodiimide was added to the mixture and made to react for the period shown below, then 2 ml of an aqueous acetic acid-sodium acetate buffer solution was added to stop the reaction. The reaction mixture was dialyzed against 5 liters of distilled water for 72 hours at a temperature of 4° C. (during the dialysis, the external liquid was exchanged every 24 hours). After condensing the internal liquid, it was passed through a column of 1.5 cm in diameter and 55 cm in height packed with a derivative of dextrin (Sephadex G-25, made by Pharmacia Japan Co., Ltd.) to absorb the low-molecular weight substances in the reaction mixture completely onto the column and the effluent was freeze-dried at a temperature of −20° C. to obtain the object substance. The bonded amount of cytarabine as the function of reaction period presumed by the separately carried out results of bio assay are shown in Table 19.

TABLE 19

| Period of reaction (min) | Cytarabine (microgram)/antibody (mg) |
|---|---|
| 10 | 4.8 |
| 30 | 8.2 |
| 60 | 11.0 |

SYNTHETIC EXAMPLE 7

Into an aqueous solution containing 10 mg of rabbit's antibody against P-388 tumor (cancer) prepared and purified in 8-1 of Example 8 in one ml, 6.0 mg of methotrexate was added and while adjusting the pH of the solution to 4.75 by the addition of hydrochloric acid under agitation 2.5 mg of 1-ethyl-3-(3-dimethylaminopropyl)carbodiimide hydrochloride was added to make reaction for the period shown below. The reaction was then stopped by the addition of 2 ml of an aqueous acetic acid-sodium acetate buffer solution. The reaction mixture was dialyzed against 5 liters of distilled water for 72 hours at a temperature of 4° C. (during the dialysis, the external liquid was exchanged every 24 hours).

The dialyzed internal liquid was treated as in Synthetic Example 6 above to obtain the object pharmaceutical composition. The amount of bonded methotrexate was shown in Table 20 as a function of reaction period.

TABLE 20

| Period of reaction (min) | Methotrexate (microgram/antibody) (mg) |
|---|---|
| 10 | 3.6 |
| 30 | 6.5 |
| 90 | 15.0 |

SYNTHETIC EXAMPLE 8

Bonding 5-fluorouracil to the antibody

Using the rabbit's antibody against P-388 tumor (cancer) prepared and purified in 8-1 of Example 8 and 34.7 mg of 5-fluorouracil, a reaction was carried out in the same manner as is Synthetic Example 7, however, the obtained product substantially did not contain 5-fluorouracil moiety. Then, after introducing a carboxyl group into 5-fluorouracil by the following procedure, the bonding reaction was performed in the same manner as in 8-1, Example 8. The thus obtained bonded pharmaceutical composition contained 10 microgram of 5-fluorouracil per mg of the antibody.

The carboxylated 5-fluorouracil was synthesized as follows:

To 10 ml of methanol, 500 mg of 5-fluorouracil and 86 mg of potassium hydroxide were added and 3 ml of distilled water was added to the mixture. To the thus formed transparent liquid, 145 mg of chloroacetic acid were added at once and the mixture was agitated for 60 hours at the room temperature. After the reaction was over, the reaction mixture was condensed under reduced pressure and the residue was recrystallized from ethanol and chloroform to obtain 495 mg (yield of 49%) of white crystals identified as the compound having the following structure by infrared spectroscopy and elementary analysis:

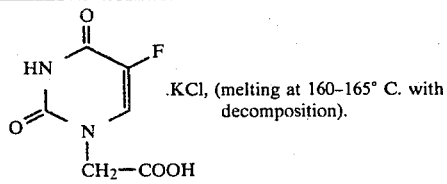

.KCl, (melting at 160–165° C. with decomposition).

| Elementary analysis: | C | H | N |
|---|---|---|---|
| Found: | 27.40% | 2.00% | 10.30% |
| Calcd as $C_6H_5N_2O_4KCl$ | 27.43 | 1.91 | 10.66 |

SYNTHETIC EXAMPLE 9

The rabbit's antibody against P-388 tumor (cancer) prepared and purified in 8-3, Example 8 was made to react with each of cytarabine, 8-azaguanine, methotrexate, aminopterin sodium and the derivative of 5-fluorouracil (refer to Synthetic Example 8) to obtain each bonded pharmaceutical composition, which was almost similar to the pharmaceutical composition obtained by Synthetic Examples 6 to 8.

EXAMPLE 9

9-1: Preparation and purification of an antibody to tumor (cancer) cells

Ascites-type P-388 tumor (cancer) cells successively cultured by using DBA/2 mice and deprived of their proliferative activity by mitomycin C were inoculated intraperitoneally into a DBA/2 mouse once a week at a rate of $10^7$ cells/animal, and after 7 days of the fourth inoculation the blood was collected from the abdominal large vein on its laparotomy under anesthesia, and the antiserum containing the antibody was prepared from the blood. Total amount of antiserum was 53 ml from 100 mice. The preparation and purification of the antibody from the antiserum were carried out in the same manner as in 8-1, Example 8.

9-2: Purification of the antibody by affinity chromatography

The lyophilized cells of ascites-type P-388 tumor (cancer) were treated in the same manner as the cells of Yoshida's sarcoma in 4-3, Example 4, however, omitting the salting-out by ammonium sulfate and the centrifugation thereafter. Thus, an aqueous solution of the antibody against ascites-type P-388 tumor (cancer) purified by affinity-chromatography was obtained.

9-3: Cytotoxicity test against tumor (cancer) cells and normal cells

Cytotoxicity due to the mouse's antibody against ascites-type P-388 tumor (cancer) obtained in 9-2 above was examined by the same method as in Example 1, the results being shown in Table 21.

TABLE 21

| Times of dilution of solution of antibody | | Mortality of Cells | | | |
|---|---|---|---|---|---|
| | | 1 | 10 | 100 | 1000 |
| Antibody before purification by affinity chromatography (1) | Cells of P-388 tumor (cancer) | +++ | ++ | — | — |
| | Splenic cells of mouse | — | — | — | — |
| Antibody after purification by affinity chromatography (1) Control (Eagle's MEM) | Cells of P-388 tumor (cancer) | +++ | +++ | ++ | + |
| | Splenic cells of mouse | — | — | — | — |
| | Cells of P-388 tumor (cancer) | — | | | |
| | Splenic cells of mouse | — | | | |

As is seen in Table 21, the activity of the antibody against P-388 tumor (cancer) cells was remarkably raised by the procedures of affinity chromatography as in the preceeding Examples.

9-4: Bonding of mouse's antibody against P-388 tumor (cancer) to anti-cancer antimetabolites The mouse's antibodies against P-388 tumor (cancer) obtained by the procedures in 9-1 and 9-2, Example 9 were respectively bonded to each of the antimetabolites, that is, cytarabine, methotrexate, aminopterin sodium, 8-azaguanine and 5-fluorouracil in the same manner as that described in 8-5, Example 8 to obtain pharmaceutical composition in which the antibody is bonded to the antimetabolite with an amide bond. These pharmaceutical composition showed almost the same physicochemical properties as those of the corresponding pharmaceutical composition obtained in 8-5, Example 5.

EXAMPLE 10

Antitumor effect (anti-cancer effect) of the pharmaceutical composition against P-388 tumor (cancer)

Cells of the P-388 tumor (cancer) cells successively cultured by using DBA/2 mice were transplanted into the abdominal cavity of each 10 DBA/2 mice of each group at a rate of $1 \times 10^6$ cells/animal, and from after 24 hours of the transplantation, an aqueous solution of each of the following antitumor substances (anti-cancer agents) was intraperitoneally administered to the mouse once a day for 5 consecutive days, in total of five times, and after observing the mortality of the mice the average survival days of treated group of mice ($\overline{T}$) and those of control (transplanted, however, not administered) ($\overline{C}$) were obtained to calculated the life-elongating rate ($100 \times \overline{T}/\overline{C}$). The results are shown in Tables 22 to 26, Table 26 showing the results of administering only the antibody.

The antitumor substances (anti-cancer agents) used in this Example are:

(1) Antimetabolic antitumor substances (anti-cancer agents): cytarabine, methotrexate, aminopterin sodium and derivative of 5-fluorouracil, (2) Bonded pharmaceutical composition of the rabbit's antibody *not purified by* affinity chromatography to one of the above-mentioned antimetabolic antitumor substances (anti-cancer agents), (3) Bonded pharmaceutical composition of the rabbit's antibody *purified by* affinity chromatography (1) to one of the above-mentioned antimetabolic antitumor substances (anti-cancer agents), (4) Bonded pharmaceutical composition of the mouse's antibody *not purified by* affinity chromatography to one of the above-mentioned antimetabolic antitumor substances (anti-cancer agents), and (5) Bonded pharmaceutical composition of the mouse's antibody *purified by* affinity chromatography (1) to one of the above-mentioned antimetabolic antitumor substances (anti-cancer agents).

TABLE 22

| Agent | | Amount of administration | | Life-elongating Rate (%) |
|---|---|---|---|---|
| | | Agent (mg/kg) | Cytarabine (mg/kg) | |
| Cytarabine | | 20 | 20 | 220 |
| Present Composition | Rabbit's Antibody | 200 | 2 | 200 |
| | *Rabbit's Antibody | 200 | 2 | 210 |
| | Mouse's Antibody | 200 | 2 | 210 |
| | *Mouse's Antibody | 200 | 2 | 215 |

Note:
*indicates that the antibody has been purified by affinity chromatography (1).

TABLE 23

| Agent | | Amount of administration | | Life-elongating Rate (%) |
|---|---|---|---|---|
| | | Agent (mg/kg) | Methotrexate (mg/kg) | |
| Methotrexate | | 3 | 3 | 250 |
| Present Composition | Rabbit's Antibody | 30 | 0.3 | 190 |
| | *Rabbit's Antibody | 30 | 0.3 | 210 |
| | Mouse's Antibody | 30 | 0.3 | 230 |
| | *Mouse's Anitbody | 30 | 0.3 | 240 |

TABLE 24

| Agent | | Amount of administration | | Life-elongating Rate (%) |
|---|---|---|---|---|
| | | Agent (mg/kg) | Aminopterin sodium (mg/kg) | |
| Aminopterin sodium | | 3 | 3 | 270 |
| Present Composition | Rabbit's Antibody | 30 | 0.3 | 240 |
| | *Rabbit's Antibody | 30 | 0.3 | 245 |
| | Mouse's Antibody | 30 | 0.3 | 250 |
| | *Mouse's Antibody | 30 | 0.3 | 260 |

TABLE 25

| Agent | | Amount of administration | | Life-elongating Rate (%) |
|---|---|---|---|---|
| | | Agent (mg/kg) | A derivative of 5-fluoro-uracil (mg/kg) | |
| A derivative of 5-fluorouracil | | 50 | 50 | 185 |
| Present Composition | Rabbit's Antibody | 500 | 5 | 160 |
| | *Rabbit's Antibody | 500 | 5 | 170 |
| | Mouse's Antibody | 500 | 5 | 165 |
| | *Mouse's Antibody | 500 | 5 | 180 |

TABLE 26

| Antibody | Dose rate (mg/kg) | Life-elongating rate (%) |
|---|---|---|
| Rabbit* | 5 | 100 |
| | 5 | 105 |
| Rabbit* | 20 | 105 |
| | 20 | 105 |
| Mouse* | 5 | 110 |

TABLE 26-continued

| Antibody | Dose rate (mg/kg) | Life-elongating rate (%) |
|---|---|---|
| | 5 | 120 |
| Mouse* | 20 | 120 |
| | 20 | 120 |

Note:
*Shows that the antigen was purified by affinity chromatography (1)

The characteristic feature of the pharmaceutical composition does at first appear when the amount of administration of the commercial antitumor substance (anti-cancer agent) itself is compared to the amount of administration of the same antitumor substance (anti-cancer agent) as a component of the pharmaceutical composition. In spite of the fact that the latter is only one tenth to one twentieth of the former, the life-elongating rate due to the latter is almost equal to that due to the former. The fact is the reflection of the phenomenon that the antibody favorably transfers the commercial antitumor substance (anti-cancer agent) to the tumor (cancer) site in the animal body, and the excellent realization of the idea of the present invention. The pharmaceutical composition, owing to the above-mentioned function, exhibits its antitumor activity (anti-cancer activity) to the same degree as the commercial antitumor substance (anti-cancer agent) having an extremely high side effects while reducing the use of such a commercial antitumor substance (anti-cancer agent) to one tenth-one twentieth.

In addition, it should be especially noticed that in the case where the antibody prepared by using rabbit is bonded to each of the commercial antitumor substances (anti-cancer agents) and administered to mice, anaphylactic shock such as general spasm and stiffening appears on among 3 mice among 10 mice, however, the pharmaceutical composition produced by bonding the same antitumor substance (anti-cancer agent) with the antibody prepared by using rabbit and purified by affinity chromatography does not appear substantially such anaphylactic shocks. The pharmaceutical composition produced by bonding the antibody prepared by using mouse and purified by affinity chromatography with the same commercial antitumor substance (anti-cancer agent) never gave such anaphylactic shocks. These findings have been experienced already in Examples 3 and 6, and the reason is the reflection of the effectiveness of the affinity chromatography in removing the cause of such anaphylactic shock.

EXAMPLE 11

(A-1) Synthesis of N-acylated antibiotic

As the antibiotic, daunorubicin hydrochloride and mitomycin C were respectively used.

Into an ice-cooled solution of 100 mg of daunorubicin hydrochloride dissolved in 10 ml of water, 1 ml of acetic anhydride was added, and the mixture were stirred for a night. Then, the mixture was extracted 3 times with each 20 ml of ethyl acetate, and after dehydrating the extract on anhydrous sodium sulfate, the extract was condensed to obtain 90 mg of raw crystals. By recrystallizing the crystals from a mixture of ethyl acetate and n-hexane, 75 mg of purified N-acetyl-daunorubicin hydrochloride.

In the same manner, from starting mitomycin, C, N-acetylmitomycin C was obtained.

(A-2) Reaction of the antibody and the N-acetylated antibiotic

Into an aqueous solution of 10.4 mg of the rabbit's anti-sarcoma 180 antibody which has been purified by affinity chromatography dissolved in 1 ml of water, 13 mg of N-acetyldaunorubicin hydrochloride obtained in (A-1) was added. After adjusting the pH of the mixture with hydrochloric acid under agitation to 4.75, and further adding 3.75 mg of 1-ethyl-3-(3-dimethylaminopropyl)carbodiimide hydrochloride to the mixture, the mixture was stirred for 60 min. and then the reaction was stopped by the addition of 2 ml of an aqueous solution of acetic acid and sodium acetate of pH of 4.70. The reaction product was then subjected to dialysis against 5 liters of distilled water at 4° C. for 72 hours.

(A-3) Determination of the optical density of the reaction product

After condensing the dialyzate (internal liquid in the dialyzing pouch), the condensate was fractioned by gel-filtration in a column of 1.5 cm in diameter and 55 cm in height filled with Sephadex G-25. The fractions, each 3 ml, were determined on their optical density by the respective two ultraviolet lights, of 280 nm (for the original antibody) and 480 nm (for the original daunorubicin hydrochloride or the N-acetyldaunorubicin hydrochloride).

The thus obtained pattern of optical density of the fractions of the reaction product between the antibody and N-acetylated daunorubicin hydrochloride is shown in the solid line in FIG. 9.

The same procedures of synthesizing N-acetylmitomycin C, reacting N-acetylmitomycin C with the antibody and determination of the optical density of fractions of the reaction product were carried out in the same manner as above, and the pattern of optical density of the fractions of reaction products is shown in FIG. 11, however using the ultraviolet light of 360 nm. (B) The reaction for condensation was carried out between the same antibody and the original antibiotic (not-acetylated), and the procedures of dialysis, gel-filtration and determination of the optical density of the fractions of the reaction product were carried out in the same manner as in (A-1) and (A-2) to obtain the pattern of optical density of the fractions of the reaction product shown in FIG. 10 (reaction product between the antibody and daunorubicin hydrochloride) and FIG. 12 (reaction product between the antibody and mitomycin C).

The pattern of optical density of the fractions of the antibody itself was quite the same as that shown in the solid lines in FIG. 9, and accordingly not shown herein. The pattern of optical density of each of the antibiotics (taken by 480 nm on daunorubicin hydrochloride and on N-acetyldaunorubicin hydrochloride, and by 360 nm on mitomycin C and on N-acetylmitomycin C) was not shown herein on the same reason.

(C) Antitumor effect (anti-cancer effect) of the pharmaceutical composition against sarcoma 180 solid tumor (cancer)

From the following Table 27, it is clearly recognized that the active ingredient of the present invention, especially the purified anti-sarcoma 180 antibody bonded with mitomycin C was effective almost equally to mitomycin C itself with the amount of administration of only one twentieth of that of mytomycin C itself, and the purified anti-sarcoma 180 antibody bonded with daunorubicin hydrochloride was effective almost equally to daunorubicin hydrochloride itself with the amount of administration of only one tenth of that of daunorubicin hydrochloride itself. On the other hand, in the case where each of the antibiotics was mixed with the purified antibody and the mixture was administered, the effect was only about the half of the effect of the purified antibody bonded with one of the antibiotics.

(D) Pyrogenetic anaphylaxis test

One hundred guinea pigs were divided into 10 groups (ten animals per group), and each of the substances shown in the following table was administered to each animal of each group at a rate of 50 mg/kg subcutaneously 5 times per week (as one cycle) for 4 cycles for sensitization.

TABLE 27

Antitumor (anti-cancer) effect of the active ingredient of the present invention expressed by Rate of inhibiting the proliferation of transplanted cells of solid type sarcoma 180 tumor (cancer) (%)

| Agent administered | Administered amount (mg/kg) of the agent | Administered amount of the agent as antibiotic (mg/kg) | Effect of inhibiting the proliferation of tumor (cancer) cells | Remarks |
|---|---|---|---|---|
| Mitomycin C only | 1 | 1 | 40 | |
| Mitomycin C bonded with Rabbit's antibody (catalyst)* | 5 | 0.05 | 32 | |
| Mitomycin C bonded with Rabbit's antibody $A_1$ (catalyst)* | 5 | 0.05 | 40 | Present invention |
| Mitomycin C bonded with Mouse's antibody (catalyst)* | 5 | 0.05 | 39 | |
| Mitomycin C bonded with Mouse's antibody $A_1$ (catalyst)* | 5 | 0.05 | 40 | Present invention |
| Mitomycin C subjected to binding to Rabbit's antibody in the absence of catalyst | 5 | 0 (not detected) | 15 | Comparison |
| Mitomycin C subjected to binding to Rabbit's antibody $A_1$ in the absence of catalyst | 5 | 0 (not detected) | 17 | Comparison |
| Mitomycin C was merely admixed with Mouse's antibody | 5 | 0.05 | 16 | Comparison |
| Mitomycin C was merely admixed with Mouse's antibody $A_1$ | 5 | 0.05 | 20 | Comparison |
| Daunorubicin hydrochloride only | 0.5 | 0.5 | 45 | Comparison |

TABLE 27-continued

Antitumor (anti-cancer) effect of the active ingredient of the present invention expressed by Rate of inhibiting the proliferation of transplanted cells of solid type sarcoma 180 tumor (cancer) (%)

| Agent administered | Administered amount (mg/kg) of the agent | Administered amount of the agent as antibiotic (mg/kg) | Effect of inhibiting the proliferation of tumor (cancer) cells | Remarks |
|---|---|---|---|---|
| Daunorubicin hydrochloride bonded with Rabbit's antibody (catalyst) | 5 | 0.05 | 35 | Comparison |
| Daunorubicin hydrochloride bonded with Rabbit's antibody $A_1$ (catalyst) | 5 | 0.05 | 43 | Present invention |
| Daunorubicin hydrochloride bonded with Mouse's antibody (catalyst) | 5 | 0.05 | 44 | Present invention |
| Daunorubicin hydrochloride bonded with Mouse's antibody $A_1$ (catalyst) | 5 | 0.05 | 45 | Present invention |
| Daunorubicin hydrochloride subjected to binding to Rabbit's antibody in the absence of catalyst | 5 | 0 (not detected) | 18 | Comparison |
| Daunorubicin hydrochloride subjected to binding to Rabbit's antibody $A_1$ | 5 | 0 (not detected) | 20 | Comparison |
| Duanorubicin hydrochloride merely admixed with Mouse's antibody | 5 | 0.05 | 19 | Comparison |
| Daunorubicin hydrochloride merely admixed with Mouse's antibody $A_1$ | 5 | 0.05 | 23 | Comparison |

Note:
(catalyst)*means that the reaction of mitomycin C and the antibody was carried out in the presence of a carbodiimide as the catalyst.
Antibody $A_1$ means that the antibody was purified by affinity chromatography (1) shown at page 6, lines 14 to 24.

After 2 weeks of the ending of sentitization, the same substance was administered at a rate of 10 mg/kg b.w. intravenously 2 times at an interval of 2 weeks as the inducing procedure. The results of the induction of pyrogenetic anaphylaxis are shown also in the Table 28. As are seen in the results in the Table 28, the active ingredient of the pharmaceutical composition of the present invention only gave a remarkably reduced pyrogenetic anaphylaxis.

TABLE 28

| | Pyrogenetic anaphylaxis test | | |
|---|---|---|---|
| Agent administered | Amount of sensitization (mg/kg) | Amount for induction (mg/kg) | Rate of Inducing Anaphylaxis |
| Mitomycin C itself | 50 | 10 | 3/10 |
| Mitomycin C bonded with rabbit's antibody (catalyst) | 50 | 10 | 2/10 |
| Mitomycin C bonded with rabbit's purified antibody $A_1$ (catalyst) | 50 | 10 | 0/10 Present invention |
| Mitomycin C bonded with mouse's antibody (catalyst) | 50 | 10 | 1/10 |
| Mitomycin C bonded with mouse's purified antibody $A_1$ (catalyst) | 50 | 10 | 0/10 Present invention |
| Daunorubicin hydrochloride bound to rabbit's antibody (catalyst) | 50 | 10 | 2/10 |
| Daunorubicin hydrochloride bound to rabbit's purified antibody $A_1$ (catalyst) | 50 | 10 | 0/10 Present invention |
| Daunorubicin hydrochloride bound to mouse's antibody (catalyst) | 50 | 10 | 1/10 |
| Daunorubicin hydrochloride bound to mouse's purified antibody $A_1$ (catalyst) | 50 | 10 | 0/10 Present invention |
| Daunorubicin hydrochloride itself | 50 | 10 | 3/10 |

EXAMPLE 12

From the serum obtained from a male patient of age of 50 suffering from the cancer of the rectum, 2000 ml of an antiserum containing an anticancer-antibody was obtained, and by subjecting the antibody to salting out with ammonium sulfate, a fraction containing immunoglobulin was collected.

By carrying out an affinity-chromatography on the fraction following the method in Example 7(7-2), the anticancer-antibody was obtained in a pure state.

Doxorubicin hydrochloride was brought into reaction with the thus purified anticancer-antibody for 40 min at a pH of 5.25 to obtain the anticancer-antibody bonded to adriamycin, and the product was purified by using Sephadex G-200 column (14 cm in diameter and 145 cm in height) while using a physiological saline solution as the eluent.

To the patent, 320 ml of the eluate containing 3.2 g of the anticancer-antibody bonded to 19.2 mg of doxorubicin hydrochloride was administered by intravenous drip.

No side reactions including depilation which is usually observed in cases where doxorubicin hydrochloride is administered were observed on the thus treated patient confirming the safety of the medicine, and moreover, the proliferation of the cancer of the rectum was suspended with a tendency of reduction in size. Then the treatment was continued with the administration of 30 mg of doxorubicin hydrochloride. In this treatment, depilation was observed.

What is claimed is:

1. A pharmaceutical composition is dosage unit form for use in the treatment of cancer, which comprises a therapeutically effective amount of a substance bonded by amide bonding an anti-cancer drug having at least one amino group or carboxyl group, selected from the group consisting of antibiotic substances, antimetabolitic substances and alkylating agents with an anti-cancer antibody obtained by purifying immunogloubulin fraction with affinity-chromatography, in the presence of a reagent selected from the group consisting of thionyl chloride, diethyl phosphorocyanidate and a carbodiimide, and a pharmaceutically acceptable carrier.

2. A pharmaceutical composition according to claim 1, wherein said antibiotic substance is selected from the group consisting of mitomycin C, doxorubicin hydrochloride, bleomycin, daunorubicin, actinomycin D and sarkomycin.

3. A pharmaceutical composition according to claim 1, wherein said antimetabolitic substance is selected from the group consisting of cytarabine, 8-azaguanine, 5-fluorouracil, methotrexate and sodium aminopterin.

4. A pharmaceutical composition according to claim 1, wherein said alkylating agent is selected from the group consisting of chlorambucil, melphalan, uramustine, ACNU and cyclophosphamide.

5. A pharmaceutical composition according to claim 1, wherein said anti-cancer antibody is an anti-cancer alloantibody purified by affinity-chromatography.

6. A pharmaceutical composition according to claim 1, wherein the amino group or the carboxyl group of said anti-cancer drug is introduced thereinto by bringing the anti-cancer drug into reaction with a compound having the formula:

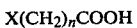
$$X(CH_2)_nCOOH$$

wherein X represents an atom of chlorine or bromine and n denotes an integer of 1 to 3.

7. A pharmaceutical composition according to claim 1, wherein the amino group or the carboxyl group of said anti-cancer drug is introduced thereinto by bringing the anti-cancer drug into reaction with a compound having the formula:

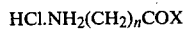
$$HCl \cdot NH_2(CH_2)_nCOX$$

wherein X represents an atom of chlorine or bromine and n denotes an integer of 1 to 3.

8. A pharmaceutical composition according to claim 1, wherein said affinity-chromatography is performed by using a carrier to which molecules of the cancer antigen are bound.

9. A pharmaceutical composition according to claim 8, wherein said carrier is packed into a column.

* * * * *